US007300405B2

(12) United States Patent
Guion et al.

(10) Patent No.: US 7,300,405 B2
(45) Date of Patent: Nov. 27, 2007

(54) ANALYSIS OF AUSCULTATORY SOUNDS USING SINGLE VALUE DECOMPOSITION

(75) Inventors: Marie A. Guion, St. Paul, MN (US); Arthur G. Erdman, New Brighton, MN (US); George Sommerfeld, Brainerd, MN (US); Ahmed H. Tewfik, Edina, MN (US); Craig D. Oster, Oakdale, MN (US)

(73) Assignees: 3M Innovative Properties Company, St. Paul, MN (US); Regents of the University of Minnesota, Minneapolis, MN (US)

( * ) Notice: Subject to any disclaimer, the term of this patent is extended or adjusted under 35 U.S.C. 154(b) by 540 days.

(21) Appl. No.: 10/781,118

(22) Filed: Feb. 18, 2004

(65) Prior Publication Data

US 2005/0090755 A1    Apr. 28, 2005

Related U.S. Application Data

(60) Provisional application No. 60/513,444, filed on Oct. 22, 2003.

(51) Int. Cl.
*A61B 5/02* (2006.01)
*A61B 7/02* (2006.01)
*A61B 7/04* (2006.01)

(52) U.S. Cl. .................. 600/528; 181/131; 381/67
(58) Field of Classification Search ............... 600/528; 381/67; 181/131
See application file for complete search history.

(56) References Cited

U.S. PATENT DOCUMENTS 3,878,832 A    4/1975  Tickner et al.

| 4,094,308 A | 6/1978 | Cormier |
| 4,154,231 A | 5/1979 | Russell |
| 4,193,393 A | 3/1980 | Schlager |
| 4,220,160 A | 9/1980 | Kimball et al. |

(Continued)

FOREIGN PATENT DOCUMENTS

WO    90/08503    8/1990

(Continued)

OTHER PUBLICATIONS

Leonard Karpman, M.D., John Cage, Charles Hill, A.D. Forbes, Valerie Karpman, Keith Cohn, MD, F.A.C.C., "Sound Envelope Averaging and the Differential Diagnosis of Systolic Murmurs," American Heart Journal, vol. 90, pp. 600-606, 1975.

(Continued)

*Primary Examiner*—George Manuel
*Assistant Examiner*—Christopher A. Flory
(74) *Attorney, Agent, or Firm*—Shumaker & Sieffert, P.A

(57) ABSTRACT

Techniques are described for analyzing auscultatory sounds to aid a medical professional in diagnosing physiological conditions of a patient. A data analysis system, for example, applies singular value decomposition to auscultatory sounds associated known physiological conditions to define a set of one or more disease regions within a multidimensional space. A diagnostic device, such as an electronic stethoscope or personal digital assistant, applies configuration data from the data analysis system to generate a set of one or more vectors within the multidimensional space representative of auscultatory sounds associated with a patient. The diagnostic device outputs a diagnostic message associated with a physiological condition of the patient based on the orientation of the vectors relative to the disease regions within the multidimensional space.

53 Claims, 12 Drawing Sheets

U.S. PATENT DOCUMENTS

| | | | |
|---|---|---|---|
| 4,289,141 | A | 9/1981 | Cormier |
| 4,446,873 | A | 5/1984 | Groch et al. |
| 4,546,777 | A | 10/1985 | Groch et al. |
| 4,548,204 | A | 10/1985 | Groch et al. |
| 4,549,551 | A | 10/1985 | Dyck et al. |
| 4,549,552 | A | 10/1985 | Groch et al. |
| 4,672,976 | A | 6/1987 | Kroll |
| 4,679,570 | A | 7/1987 | Lund et al. |
| 4,712,565 | A | 12/1987 | Katz et al. |
| 4,720,866 | A | 1/1988 | Elias et al. |
| 4,792,145 | A | 12/1988 | Eisenberg et al. |
| 4,889,130 | A | 12/1989 | Lee |
| 4,905,706 | A | 3/1990 | Duff et al. |
| 4,967,760 | A | 11/1990 | Bennett, Jr. et al. |
| 5,025,809 | A | 6/1991 | Johnson et al. |
| 5,036,857 | A | 8/1991 | Semmlow et al. |
| 5,109,863 | A | 5/1992 | Semmlow et al. |
| 5,213,108 | A | 5/1993 | Bredesen et al. |
| 5,218,969 | A | 6/1993 | Bredesen et al. |
| 5,301,679 | A | 4/1994 | Taylor |
| 5,360,005 | A | 11/1994 | Wilk |
| 5,490,516 | A | 2/1996 | Hutson |
| 5,687,738 | A | 11/1997 | Shapiro et al. |
| 6,048,319 | A | 4/2000 | Hudgins et al. |
| 6,053,872 | A | 4/2000 | Mohler |
| 6,135,966 | A | 10/2000 | Ko |
| 6,396,931 | B1 | 5/2002 | Malilay |
| 6,440,082 | B1 | 8/2002 | Joo et al. |
| 2002/0058889 | A1 | 5/2002 | Lee |
| 2004/0207625 | A1* | 10/2004 | Griffin et al. ............... 345/440 |
| 2004/0208390 | A1* | 10/2004 | Jiang et al. .................. 382/260 |
| 2004/0209237 | A1* | 10/2004 | Flewelling et al. ............ 435/4 |

FOREIGN PATENT DOCUMENTS

| | | |
|---|---|---|
| WO | 00/02486 | 1/2000 |
| WO | 02/096293 | 12/2002 |

OTHER PUBLICATIONS

Rangaraj M. Rangayya, Richard J. Lehner, "Phonocardiogram Signal Analysis: A Review," Critical Reviews in Bomedical Engineering, vol. 15, Issue 3, pp. 211-236, 1988.

Masashi Yokoi, M.D., Zen-ichiro Uozumi, M.D., Noboru Okamoto, M.D., Yoshiko Mizuno, M.D., Toru Iwatsuka, M.D., Haruo Takahashi, M.D., Yoshihiko Watanabe, M.D., Shoji Yasui, M.D., "Clinical Evaluation on 5 Years' Experience of Automated Phonocardiographic Analysis," Japan Heart Journal, vol. 18, pp. 482-490, 1977.

C. Longhini, M.D., F. Portaluppi, M.D., E. Arslan, M.D., F. Pedrielli, M.S., "The Fast Fourier Transform in the Analysis of the Normal Phonocardiogram," Japanese Heart Journal, vol. 20, No. 3, pp. 333-339, May 1979.

Louis-Gilles Durand, Philippe Pibarot, "Digital Signal Processing of the Phonocardiogram: Review of the Most Recent Advancements." Critical Reviews in Biomedical Engineering, vol. 23, Issue (3/4), pp. 163-219, 1995.

Messer S.R., Agzarian J., Abbott D., "Optimal Wavelet Denoising for Phonocardiograms," Microelectronics Journal, vol. 32, pp. 931-941, 2001.

Louis-Gilles Durand, Michel Blanchard, Guy Cloutier, Hani N. Sabbah, Paul D. Stein, "Comparison of Pattern Recognition Methods for Computer-Assisted Classification of Spectra of Heart Sounds in Patients with a Porcine Bioprosthetic Valve Implanted in the Mitral Position," IEEE Transactions on Biomedical Engineering, vol. 37, No. 12, pp. 1121-1129, Dec. 1990.

Curt G. DeGroff, M.D., Sanjay Bhatikar, Ph.D., Jean Hertzberg Ph.D., Robin Shandas, Ph.D., Lilliam Valdes-Cruz, M.D., Roop L. Mahajan, Ph.D., "Artificial Neural Network-Based Method of Screening Heart Murmurs in Children," Circulation, pp. 2711-2716, Jun. 5, 2001.

Michael Schroeder, "Using Singular Valve Decomposition to Visualise Relations Within Multi-Agent Systems," In Proceedings of the Third Conference on Autonomous Agents, Seattle, USA: ACM Press, pp. 313-318, 1999.

J. Semmlow, W. Welkowitz, J. Kostis, and J.W. Mackenzie, "Coronary Artery Disease—Correlates Between Diastolic Auditory Characteristics and Coronary Artery Stenoses," IEEE Transactions on Biomedical Engineering, vol. BME-30, No. 2, pp. 136-139, Feb. 1983.

H.P. Sava et al., "Spectral Analysis of Carpentier-Edwards Prosthetic Heart Valve Sounds in the Aortic Position Using SVD-Based Methods," IEE Colloquim on Signal Processing in Cardiography, pp. 6-1-6-4, 1995.

T. Olmez et al., "Classification of Heart Sounds Using an Artificial Neural Network," Pattern Recognition Letters, vol. 24, No. 1-3, pp. 617-629, Jan. 2003.

S.M. Lee et al., "Heart Sound Recognition by New Methods Using the Full Cardiac Cycled Sound Data," IEICE Transactions on Information and Systems, Institute of Electronics Information and Communication Engineering, Tokyo, JP, vol. E84-D, No. 4, pp. 521-529, Apr. 2001.

Written Opinion of the International Application No. PCT/US2004/034557, mailed Feb. 24, 2005.

International Search Report for International Application No. PCT/US2004/034557, mailed Feb. 24, 2005.

M. Akay et al., "Application of the ARMA Method to Acoustic Detection of Coronary Artery Disease," Medical & Biological Engineering & Computing, pp. 365-372, Jul. 1991.

J.R. Bulgrin et al., "Comparison of Short-Time Fourier, Wavelet and Time-Domain Analyses of Intracardiac Sounds," Biomedical Sciences Instrumentaiton, vol. 29, pp. 465-472, 1993.

J.Chambers, "The Clinical and Diagnostic Features of Mitral Valve Disease," Hospital Medicine, vol. 62, No. 2, pp. 72-78, Feb. 2001.

S.G. Chang et al., "Wavelet Thresholding for Multiple Noisy Image Copies," IEEE Transactions on Image Processing, vol. 9, No. 9, pp. 1631-1635, Sep. 2000.

V. Chervassky et al., "Myopotential Denoising of ECG Signals Using Wavelet Thresholding Methods," Neural Networks, vol. 14, pp. 1129-1137, 2001.

M. Cozic et al., "Development of a Cardiac Acoustic Mapping System," Medical & Biological Engineering & Computing, pp. 431-437, Jul. 1998.

C.G. DeGroff et al., "Artificial Neural Network-Based Method of Screening Heart Murmurs in Children," Circulation, pp. 2711-2716, Jun. 5, 2001.

R.L. Donnerstein, "Continuous Spectral Analysis of Heart Murmurs for Evaluating Stenotic Cardiac Lesions," The American Journal of Cardiology, vol. 64, pp. 625-630, Sep. 15, 1989.

L.G. Durand et al., "Comparison of Spectral Techniques for Computer-Assisted Classification of Spectra of Heart Sounds in Patients with Porcine Bioprosthetic Valves," Medical & Biological Engineering & Computing, pp. 229-236, May 1993.

L.J. Hadjileontiadis et al., "A Wavelet-Based Reduction of Heart Sound Noise from Lung Sounds," International Journal of Medical Informatics, vol. 52, pp. 183-190, 1998.

J.A. Horiszny, "Teaching Cardiac Auscultation Using Simulated Heart Sounds and Small-Group Discussion," Family Medicine, vol. 33, No. 1, pp. 39-44, Jan. 2001.

M. Schroeder, "Using Singular Value Decomposition to Visualise Relations Within Multi-Agent Systems," Proceedings of the Third International Conference on Autonomous Agents, Seattle, USA, ACM Press, pp. 313-318, 1999.

C. Ortiz-Neu et al., "Error Patterns of 3rd Year Medical Students on the Cardiovascular Physical Examination," Teaching and Learning in Medicine, vol. 13, No. 3, pp. 161-166, 2001.

M.R. Rangaraj et al., "Quantitative Analysis of the Phonocardiogram for Detection of Murmurs," Journal of Biomedical Engineering, vol. 1, pp. 247-252, Oct. 1979.

L.G. Gamero et al., "Dectection of the First and Second Heart Sound Using Probabilistic Models," Engineering in Medicine and Biology Society, Proceedings of the 25th Annual International Conference of the IEEE, vol. 3, pp. 2877-2880, Sep. 2003.

L-G. Durand et al., "Digital Signal Processing of the Phonocardiogram: Review of the Most Recent Advancements," Critical Reviews in Biomedical Engineering, vol. 23, Issue 3/4, p. 163-219, 1995.

F. Kovacs et al., "A Rule-Based Phonocardiographic Method for Long-Term Fetal Heart Rate Monitoring," IEEE Transactions on Biomedical Engineering, vol. 47, No. 1, pp. 124-130, Jan. 2000.

P. Carson, "Problems in Auscultation," The Practioner, vol. 220, pp. 370-378, Mar. 1978.

A. Iwata et al., "Algorithm for Detecting the First and the Second Heart Sounds by Spectral Tracking," Medical & Biological Engineering and Computing, vol. 18, pp. 19-26, Jan. 1980.

R. Rangayyan et al., "Phonocardiogram Signal Analysis: A Review," Cricial Reviews in Biomedical Engineering, vol. 15, Issue 3, pp. 211-236, 1998.

M. Yokoi et al., "Clinical Evaluation on 5 Years' Experience of Automated Phonocardiographic Analysis," Japanese Heart Journal, 18, 482-490, 1977.

C. Longhini et al., "The Fast Fourier Transform in the Analysis of the Normal Phonocardiogram," Japanese Heart Journal, vol. 20, No. 3, pp. 333-339, May 1979.

A.E. Cetin et al., "Classification of Closed-and Open-Shell Pistachio Nuts Using Voice Recognition Technology," ASAE Transactions, vol. 47(2), pp. 659-664, 2004.

N. Ahmed et al., "Discrete Cosine Transform," IEEE Transactions on Computers 23(1), pp. 90-93.

I. Cathers, "Neural Network Assisted Cardiac Auscultation," Artificial Intelligence in Medicine, pp. 53-66, 1995.

A. Baskaran et al., "Fetal Heart Sound Analysis: A Preliminary Evaluation," Med. J. Malaysia, vol. 51, No. 1, pp. 64-67, Mar. 1996.

M.R. Rangaraj et al., "Quantitative Analysis of the Phonocardiogram for Detection of Murmurs," Communications, Journal of Biomedical Engineering, vol. 1, No. 4, October, 5 pages, 1979.

M. Piepoli et al., "Contribution of the Dynamic Phonocardiography to the Valvular Heart Disease Diagnosis: An Expert System Study," Acta Cardiologica, International Journal of Cardiology, vol. XLV, No. 6, pp. 521-527, 1990.

J.S. Jeffrey et al., "Application of Phonocardiography for Detecting Hypoxia-Induced Cardiovascular Adaption in the Chicken," Avian Diseases, 43, pp. 359-366, 1999.

M. Ishikawa et al., "Phonocardiographic Approach to the Detection of Right Ventricular Myodardial Infarction," Japanese Circulation Journal, vol. 54, pp. 1233-1245, Oct. 1990.

L. Khadra et al., "The Wavelet Transform and its Applications to Phonocardiogram Signal Analysis," Medical Informatics, vol. 16, No. 3, p. 271-277, 1991.

International Preliminary Report on Patentability, from corresponding PCT Application Serial No. PCT/US2004/034557, mailed Mar. 1, 2006, 10 pages.

K.S. Baydar et al., "Analysis and Classification of Respiratory Sounds by Signal Coherence Method," Proceedings of the 25$^{th}$ Annual International Conference of the IEEE EMBS, Cancun, Mexico, pp. 2950-2953, Sep. 2003.

M. El-Hanjouri et al., "Heart Disease Diagnosis Using HMM," IEEE Melecon, Cair, Egypt, pp. 489-492, May 2002.

K. Kallio et al., "Classification of Lung Sounds by Using Self-Organizing Feature Maps," Artifical Neural Networks, pp. 803-808, 1991.

R.B. Urquhart et al., "The Diagnostic Value of Pulmonary Sounds: A Preliminary Study By Computer-Aided Analysis," Computer Biol. Med., vol. 11, No. 3, 12 pages, 1981.

C.D. Bertram et al., "Correlation of Local Stretchings as a Way of Characterising Chaotic Dynamics Amid Noise," Physica D 58, 14 pages, 1992.

H. Liang et al., "Heart Sound Segmentation Algorithm Based on Heart Sound Envelogram," Computers in Cardiology, vol. 24, 2 pages, 1997.

N. Ahmed et al., "Orthogonal Transforms for Digital Signal Processing," Feature Selection in Pattern Recognition, 4 pages, 1975.

* cited by examiner

US 7,300,405 B2

ANALYSIS OF AUSCULTATORY SOUNDS USING SINGLE VALUE DECOMPOSITION

This application claims priority from U.S. Provisional Application Ser. No. 60/513,444, filed Oct. 22, 2003, the entire content of which is incorporated herein by reference.

TECHNICAL FIELD

The invention relates generally to medical devices and, in particular, electronic devices for analysis of auscultatory sounds.

BACKGROUND

Clinicians and other medical professionals have long relied on auscultatory sounds to aid in the detection and diagnosis of physiological conditions. For example, a clinician may utilize a stethoscope to monitor heart sounds to detect cardiac diseases. As other examples, a clinician may monitor sounds associated with the lungs or abdomen of a patient to detect respiratory or gastrointestinal conditions.

Automated devices have been developed that apply algorithms to electronically recorded auscultatory sounds. One example is an automated blood-pressure monitoring device. Other examples include analysis systems that attempt to automatically detect physiological conditions based on the analysis of auscultatory sounds. For example, artificial neural networks have been discussed as one possible mechanism for analyzing auscultatory sounds and providing an automated diagnosis or suggested diagnosis.

Using these conventional techniques, it is often difficult to provide an automated diagnosis of a specific physiological condition based on auscultatory sounds with any degree of accuracy. Moreover, it is often difficult to implement the conventional techniques in a manner that may be applied in real-time or pseudo real-time to aid the clinician.

SUMMARY

In general, the invention relates to techniques for analyzing auscultatory sounds to aid a medical professional in diagnosing physiological conditions of a patient. The techniques may be applied, for example, to aid a medical profession in diagnosing a variety of cardiac conditions. Example cardiac conditions that may be automatically detected using the techniques described herein include aortic regurgitation and stenosis, tricuspid regurgitation and stenosis, pulmonary stenosis and regurgitation, mitrial regurgitation and stenosis, aortic aneurisms, carotid artery stenosis and other cardiac pathologies. The techniques may be applied to auscultatory sounds to detect other physiological conditions. For example the techniques may be applied to detect sounds recorded from a patient's lungs, abdomen or other areas to detect respiratory or gastrointestinal conditions.

In accordance with the techniques described herein, singular value decomposition ("SVD") is applied to clinical data that includes digitized representations of auscultatory sounds associated with known physiological conditions. The clinical data may be formulated as a set of matrices, where each matrix stores the digital representations of auscultatory sounds associated with a different one of the physiological conditions. Application of SVD to the clinical data decomposes the matrices into a set of sub-matrices that define a set of "disease regions" within a multidimensional space.

One or more of the sub-matrices for each of the physiological conditions may then be used as configuration data within a diagnostic device. More specifically, the diagnostic device applies the configuration data to a digitized representation of auscultatory sounds associated with a patient to generate a set of one or more vectors within the multidimensional space. The diagnostic device determines whether the patient is experiencing a physiological condition, e.g., a cardiac pathology, based on the orientation of the vectors relative to the defined disease regions.

In one embodiment, a method comprises mapping auscultatory sounds associated with known physiological conditions to a set of one or more disease regions defined within a multidimensional space, and generating a set of one or more vectors within the multidimensional space representative of auscultatory sounds associated with a patient. The method further comprises outputting a diagnostic message associated with a physiological condition of the patient as a function of the vectors and the disease regions defined within the multidimensional space.

In another embodiment, a method comprises applying singular value decomposition ("SVD") to digitized representations of auscultatory sounds associated with physiological conditions to map the auscultatory sounds to a set of one or more disease regions within a multidimensional space, and outputting configuration data for application by a diagnostic device based on the multidimensional mapping.

In another embodiment, a method comprises storing within a diagnostic device configuration data generated by the application of singular value decomposition ("SVD") to digitized representations of auscultatory sounds associated with known physiological conditions, wherein the configuration data maps the auscultatory sounds to a set of one or more disease regions within a multidimensional space. The method further comprises applying the configuration data to a digitized representation representative of auscultatory sounds associated with a patient to select one or more of the physiological conditions; and outputting a diagnostic message indicating the selected physiological conditions.

In another embodiment, a diagnostic device comprises a medium and a control unit. The medium stores data generated by the application of singular value decomposition ("SVD") to digitized representations of auscultatory sounds associated with known physiological conditions. The control unit applies the configuration data to a digitized representation representative of auscultatory sounds associated with a patient to select one of the physiological conditions. The control unit outputs a diagnostic message indicating the selected one of the physiological conditions.

In another embodiment, a data analysis system comprises an analysis module and a database. The analysis module applies singular value decomposition ("SVD") to digitized representations of auscultatory sounds associated with known physiological conditions to map the auscultatory sounds to a set of one or more disease regions within a multidimensional space. The database stores data generated by the analysis module.

In another embodiment, the invention is directed to a computer-readable medium containing instructions. The instructions cause a programmable processor to apply configuration data to a digitized representation representative of auscultatory sounds associated with a patient to select one of a set of physiological conditions, wherein the configuration maps the auscultatory sounds to a set of one or more disease regions within a multidimensional space. The instructions further cause the programmable processor to output a diagnostic message indicating the selected one of the physiological conditions.

The techniques may offer one or more advantages. For example, the application of SVD may achieve more accurate automated diagnosis of the patient relative to conventional approaches. In addition, techniques allow configuration data to be pre-computed using the SVD, and then applied by a diagnostic device in real-time or pseudo real-time, i.e., by a clinician, to aid the clinician in rendering a diagnosis for the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
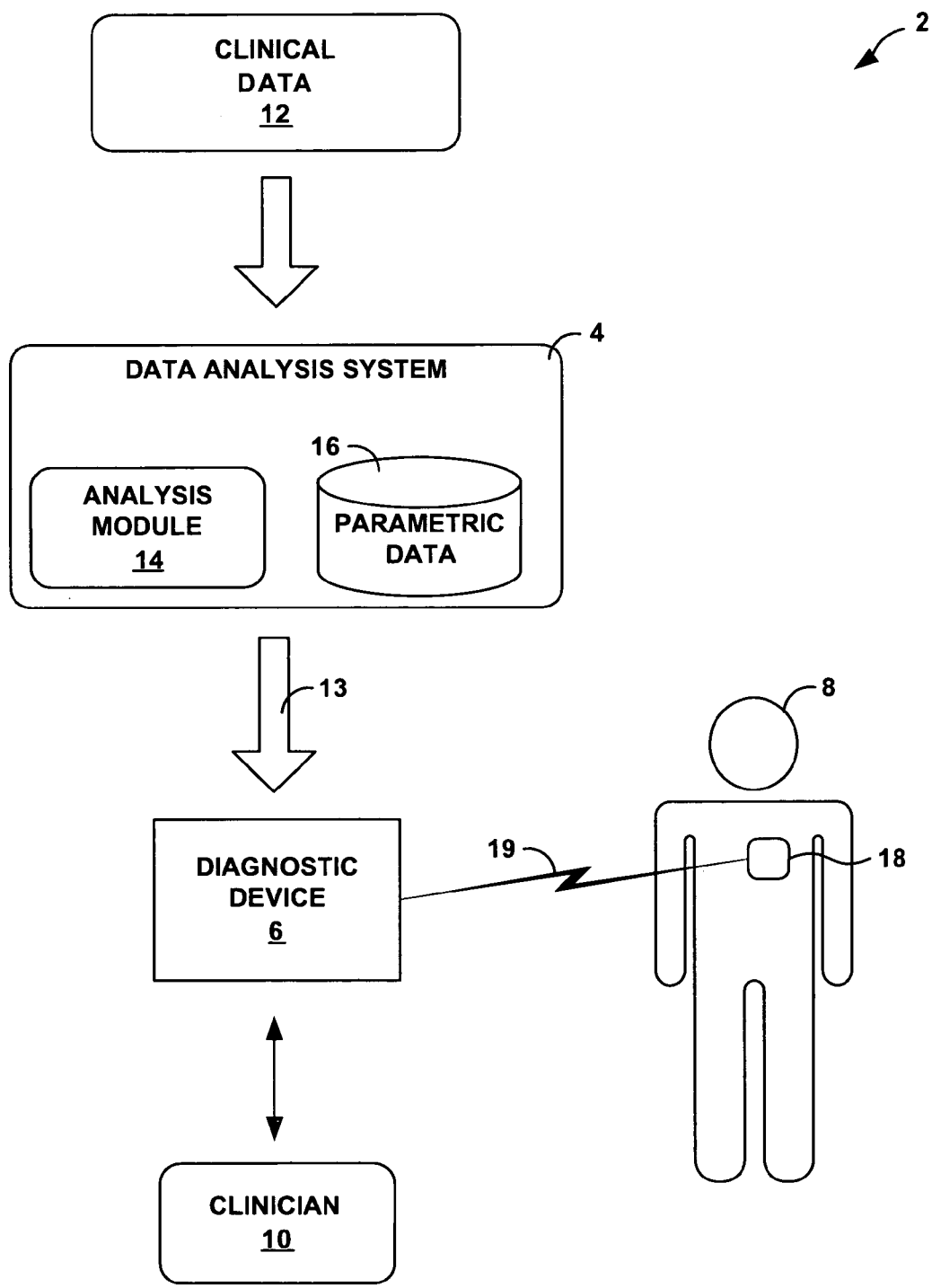
FIG. 1 is a block diagram illustrating an example system in which a diagnostic device analyzes auscultatory sounds in accordance with the techniques described herein to aid a clinician in rendering a diagnosis for a patient.

FIG. 1 is a block diagram illustrating an example system 2 in which a diagnostic device 6 analyzes auscultatory sounds from patient 8 to aid clinician 10 in rendering a diagnosis. In general, diagnostic device 6 is programmed in accordance with configuration data 13 generated by data analysis system 4. Diagnostic device 6 utilizes the configuration data to analyze auscultatory sounds from patient 8, and outputs a diagnostic message based on the analysis to aid clinician 10 in diagnosing a physiological condition of the patient. Although described for exemplary purposes in reference to cardiac conditions, the techniques may be applied to auscultatory sounds recorded from other areas of the body of patient 8. For example, the techniques may be applied to auscultatory sounds recorded from the lungs or abdomen of patient 8 to detect respiratory or gastrointestinal conditions.

In generating configuration data 13 for application by diagnostic device 6, data analysis system 4 receives and processes clinical data 12 that comprises digitized representations of auscultatory sounds recorded from a set of patients having known physiological conditions. For example, the auscultatory sounds may be recorded from patients having one or more known cardiac pathologies. Example cardiac pathologies include aortic regurgitation and stenosis, tricuspid regurgitation and stenosis, pulmonary stenosis and regurgitation, mitrial regurgitation and stenosis, aortic aneurisms, carotid artery stenosis and other pathologies. In addition, clinical data 12 includes auscultatory sounds recorded from "normal" patients, i.e., patients having no cardiac pathologies. In one embodiment, clinical data 12 comprises recordings of heart sounds in raw, unfiltered format.

Analysis module 14 of data analysis system 4 analyzes the recorded auscultatory sounds of clinical data 12 in accordance with the techniques described herein to define a set of "disease regions" within a multi-dimensional energy space representative of the electronically recorded auscultatory sounds. Each disease region within the multidimensional space corresponds to characteristics of the sounds within a heart cycle that have been mathematically identified as indicative of the respective disease.

As described in further detail below, in one embodiment analysis module 14 applies singular value decomposition ("SVD") to define the disease regions and their boundaries within the multidimensional space. Moreover, analysis module 14 applies SVD to maximize energy differences between the disease regions within the multidimensional space, and to define respective energy angles for each disease region that maximizes a normal distance between each of the disease regions. Data analysis system 4 may include one or more computers that provide an operating environment for execution of analysis module 14 and the application of SVD, which may be a computationally-intensive task. For example, data analysis system 4 may include one or more workstations or a mainframe computer that provide a mathematical modeling and numerical analysis environment.

Analysis module 14 stores the results of the analysis within parametric database 16 for application by diagnostic device 6. For example, parametric database 16 may include data for diagnostic device 6 that defines the multi-dimensional energy space and the energy regions for the disease regions with the space. In other words, the data may be used to identify the characteristics of the auscultatory sounds for a heart cycle that are indicative of normal cardiac activity and the defined cardiac pathologies. As described in further detail below, the data may comprise one or more sub-matrices generated during that application of the SVD to clinical data 12.

Once analysis module 14 has processed clinical data 12 and generated parametric database 16, diagnostic device 6 receives or is otherwise programmed to apply configuration data 13 to assist the diagnosis of patient 8. In the illustrated embodiment, auscultatory sound recording device 18 monitors auscultatory sounds from patient 8, and communicates a digitized representation of the sounds to diagnostic device 6 via communication link 19. Diagnostic device 6 applies configuration data 13 to analyze the auscultatory sounds recorded from patient 8.

In general, diagnostic device 6 applies the configuration data 13 to map the digitized representation received from auscultatory sound recording device 18 to the multi-dimensional energy space computed by data analysis system 4 from clinical data 12. As illustrated in further detail below, diagnostic device 6 applies configuration data 13 to produce a set of vectors within the multidimensional space representative of the captured sounds. Diagnostic device 6 then selects one of the disease regions based on the orientation of the vectors within the multidimensional space relative to the disease regions. In one embodiment, diagnostic device 6 determines which of the disease regions defined within the multidimensional space has a minimum distance from its representative vectors. Based on this determination, diagnostic device presents a suggested diagnosis to clinician 10. Diagnostic device 6 may repeat the analysis for one or more heart cycles identified with the recorded heart sounds of patient 8 to help ensure that an accurate diagnosis is reported to clinician 10.

In various embodiments, diagnostic device 6 may output a variety of message types. For example, diagnostic device 6 may output a "pass/fail" type of message indicating whether the physiological condition of patient 8 is normal or abnormal, e.g., whether or not the patient is experiencing a cardiac pathology. In this embodiment, data analysis system 4 may define the multidimensional space to include two disease regions: (1) normal, and (2) diseased. In other words, data analysis system 4 need not define respective disease regions with the multidimensional space for each cardiac disease. During analysis, diagnostic device 6 need only determine whether the auscultatory sounds of patient 8 more closely maps to the "normal" region or the "diseased" region, and output the pass/fail message based on the determination. Diagnostic device 6 may display a severity indicator based on a calculated distance from which the mapped auscultatory sounds of patient 8 is from the normal region.

As another example, diagnostic device 6 may output diagnostic message to suggest one or more specific pathologies currently being experienced by patient 8. Alternatively, or in addition, diagnostic device 6 may output a diagnostic message as a predictive assessment of a pathology to which patient 8 may be tending. In other words, the predictive assessment indicates whether the patient may be susceptible to a particular cardiac condition. This may allow clinician 8 to proactively prescribe therapies to reduce the potential for the predicted pathology from occurring or worsening.

Diagnostic device 6 may support a user-configurable mode setting by which clinician 10 may select the type of message displayed. For example, diagnostic device 6 may support a first mode in which only a pass/fail type message is displayed, a second mode in which one or more suggested diagnoses is displayed, and a third mode in which one or more predicted diagnoses is suggested.

Diagnostic device 6 may be a laptop computer, a handheld computing device, a personal digital assistant (PDA), an echocardiogram analyzer, or other device. Diagnostic device 6 may include an embedded microprocessor, digital signal processor (DSP), field programmable gate array (FPGA), application specific integrated circuit (ASIC) or other hardware, firmware and/or software for implementing the techniques. In other words, the analysis of auscultatory sounds from patient 8, as described herein, may be implemented in hardware, software, firmware, combinations thereof, or the like. If implemented in software, a computer-readable medium may store instructions, i.e., program code, that can be executed by a processor or DSP to carry out one of more of the techniques described above. For example, the computer-readable medium may comprise magnetic media, optical media, random access memory (RAM), read-only memory (ROM), non-volatile random access memory (NVRAM), electrically erasable programmable read-only memory (EEPROM), flash memory, or other media suitable for storing program code.

Auscultatory sound recording device 18 may be any device capable of generating an electronic signal representative of the auscultatory sounds of patient 8. As one example, auscultatory sound recording device 18 may be an electronic stethoscope having a digital signal processor (DSP) or other internal controller for generating and capturing the electronic recording of the auscultatory sounds. Alternatively, non-stethoscope products may be used, such as disposable/reusable sensors, microphones and other devices for capturing auscultatory sounds.

Application of the techniques described herein allow for the utilization of raw data in unfiltered form. Moreover, the techniques may utilize auscultatory sounds captured by auscultatory sound recording device 18 that is not in the audible range. For example, an electronic stethoscope may capture sounds ranging from 0-2000 Hz.

Although illustrated as separate devices, diagnostic device 6 and auscultatory sound recording device 18 may be integrated within a single device, e.g., within an electronic stethoscope having sufficient computing resources to record and analyze heart sounds from patient 8 in accordance with the techniques described herein. Communication link 19 may be a wired link, e.g., a serial or parallel communication link, a wireless infrared communication link, or a wireless communication link in accordance with a proprietary protocol or any of a variety of wireless standards, such as 802.11 (a/b/g), Bluetooth, and the like.

Figure 2:
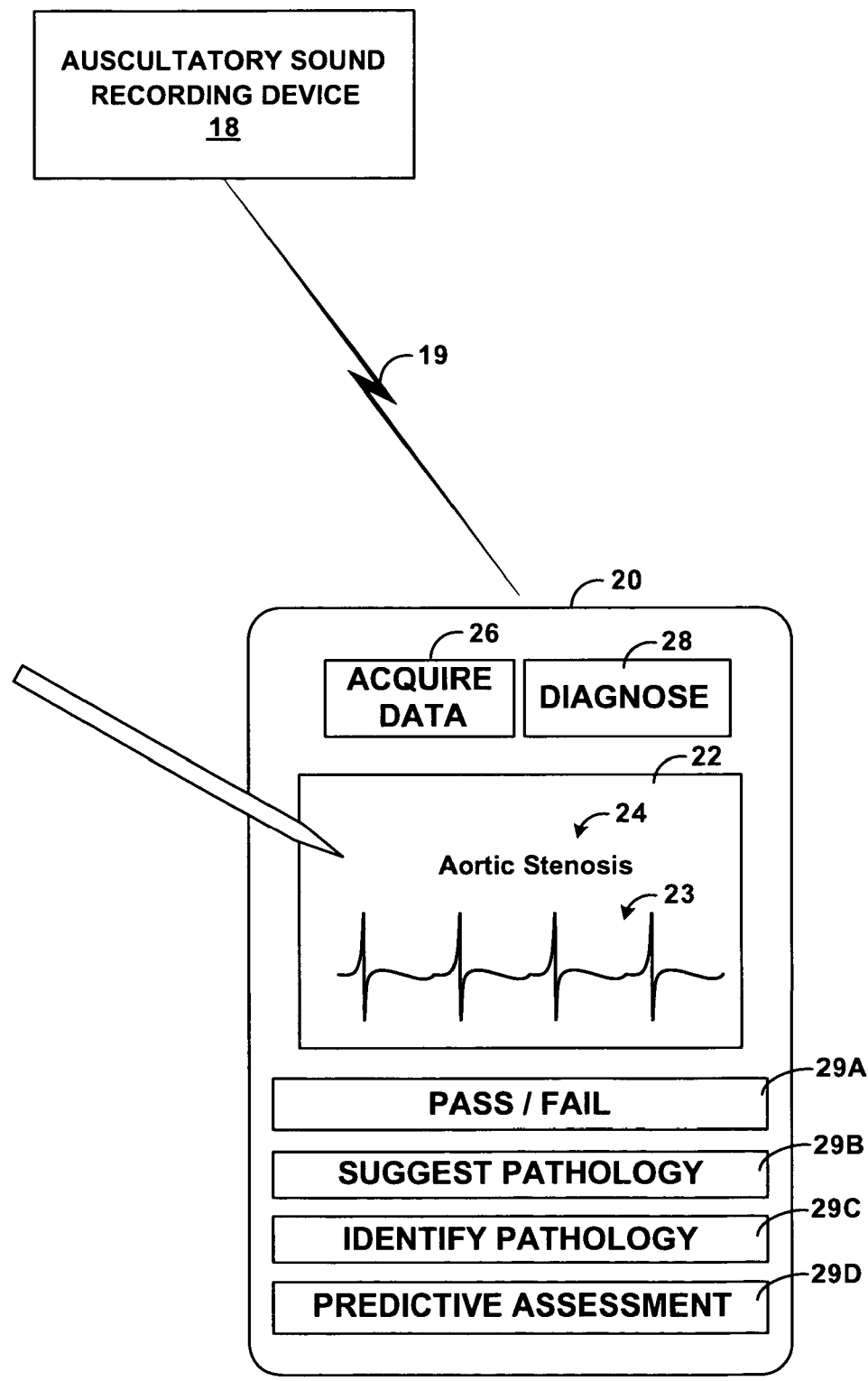
FIG. 2 is a block diagram of an exemplary embodiment of a portable digital assistant (PDA) operating as a diagnostic device in accordance with the techniques described herein.

FIG. 2 is a block diagram of an exemplary embodiment of a portable digital assistant (PDA) 20 operating as a diagnostic device to assist diagnosis of patient 8 (FIG. 1). In the illustrated embodiment, PDA 20 includes a touch-sensitive screen 22, input keys 26, 28 and 29A-29D.

Upon selection of acquisition key 26 by clinician 10, diagnostic device 20 enters an acquisition mode to receive via communication link 19 a digitized representation of auscultatory sounds recorded from patient 8. Once the digitized representation is received, clinician 10 actuates diagnose key 28 to direct diagnostic device 20 to apply configuration data 13 and render a suggested diagnosis based on the received auscultatory sounds. Alternatively, diagnostic device 20 may automatically begin processing the sounds without requiring activation of diagnose key 28.

As described in further detail below, diagnostic device 20 applies configuration data 13 to map the digitized representation received from auscultatory sound recording device 18 to the multi-dimensional energy space computed by data analysis system 4. In general, diagnostic device 20 determines to which of the disease regions defined within the multi-dimensional space the auscultatory sounds of patient 8 most closely maps. Based on this determination, diagnostic device 20 updates touch-sensitive screen 22 to output one or more suggested diagnoses to clinician 10. In this example, diagnostic device 20 outputs a diagnostic message 24 indicating that the auscultatory sounds indicate that patient 8 may be experiencing aortic stenosis. In addition, diagnostic device may output a graphical representation 23 of the auscultatory sounds recorded from patient 8.

Diagnostic device 20 may include a number of input keys 29A-29D that control the type of analysis performed via the device. For example, based on which of inputs keys 29A-29D has been selected by clinician 10, diagnostic device 20 provides a pass/fail type of diagnostic message, one or more suggested pathologies that patient 8 may currently be experiencing, one or more pathologies that patient 8 has been identified as experiencing, and/or a predictive assessment of one or more pathologies to which patient 8 may be tending.

Screen 22 or an input key could also allow input of specific patient information such as gender, age and BMI (body mass index=weight (kilograms)/height (meters) squared. This information could be used in the analysis set forth here within.

In the embodiment illustrated by FIG. 2, diagnostic device 20 may be any PDA, such as a PalmPilot manufactured by Palm, Inc. of Milpitas, Calif. or a PocketPC executing the Windows CE operating system from Microsoft Corporation of Redmond, Wash.

Figure 3:
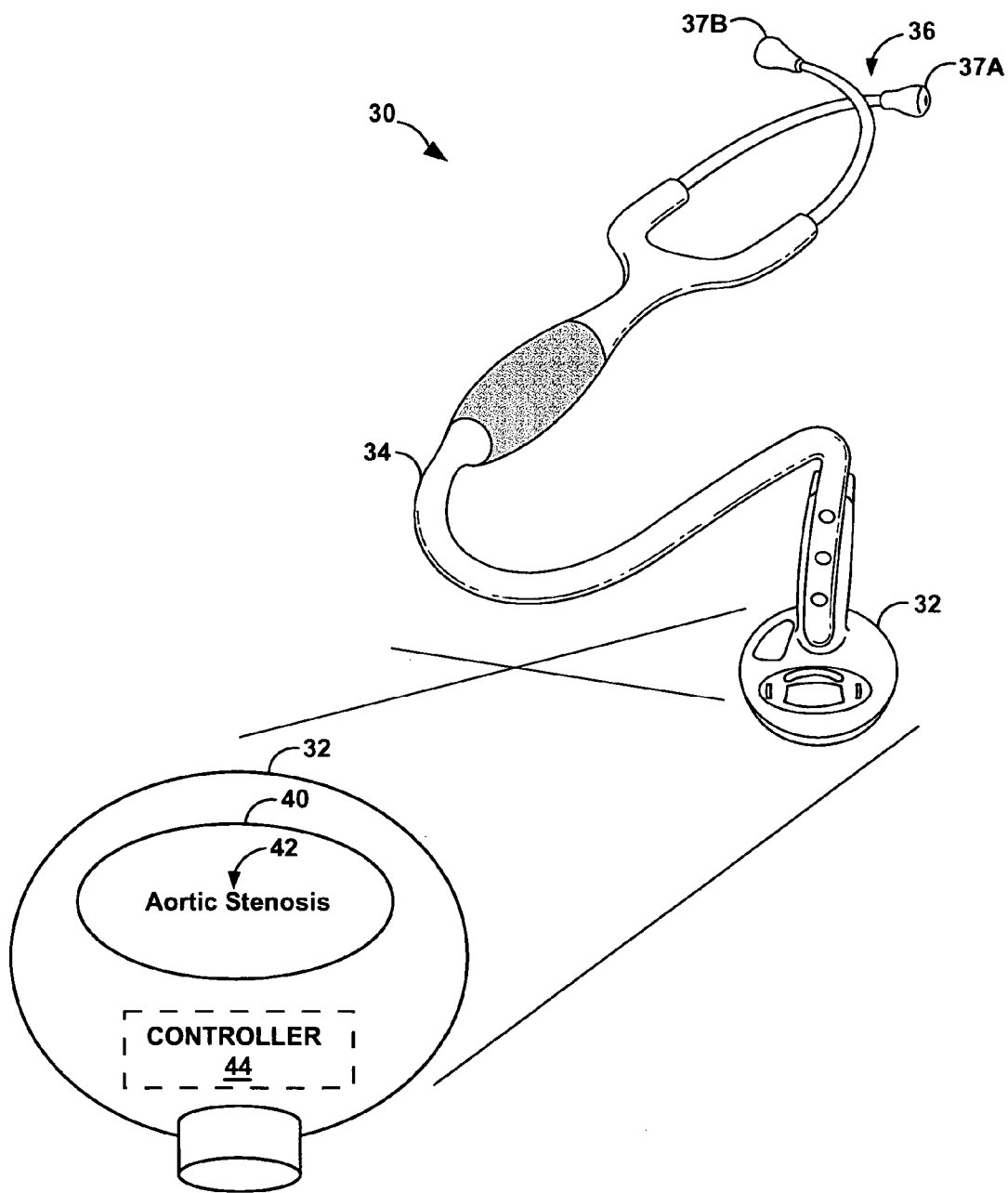
FIG. 3 is a perspective diagram of an exemplary embodiment of an electronic stethoscope operating as a diagnostic device.

FIG. 3 is a perspective diagram of an exemplary embodiment of an electronic stethoscope 30 operating as a diagnostic device in accordance with the techniques described herein. In the illustrated embodiment, electronic stethoscope 30 comprises a chestpiece 32, a sound transmission mechanism 34 and an earpiece assembly 36. Chestpiece 32 is adapted to be placed near or against the body of patient 8 for gathering the auscultatory sounds. Sound transmission mechanism 34 transmits the gathered sound to earpiece assembly 36. Earpiece assembly 36 includes a pair of earpieces 37A, 37B, where clinician 10 may monitor the auscultatory sounds.

In the illustrated embodiment, chestpiece 32 includes display 40 for output of a diagnostic message 42. More specifically, electronic stethoscope 30 includes an internal controller 44 that applies configuration data 13 to map the auscultatory sounds captured by chestpiece 32 to the multidimensional energy space computed by data analysis system 4. Controller 44 determines to which of the disease regions defined within the energy space the auscultatory sounds of patient 8 most closely maps. Based on this determination, controller 44 updates display 40 to output diagnostic message 42.

Controller 44 is illustrated for exemplary purposes as located within chestpiece 32, and may be located within other areas of electronic stethoscope 30. Controller 44 may comprise an embedded microprocessor, DSP, FPGA, ASIC, or similar hardware, firmware and/or software for implementing the techniques. Controller 44 may include a computer-readable medium to store computer readable instructions, i.e., program code, that can be executed to carry out one or more of the techniques described herein.

Figure 4:
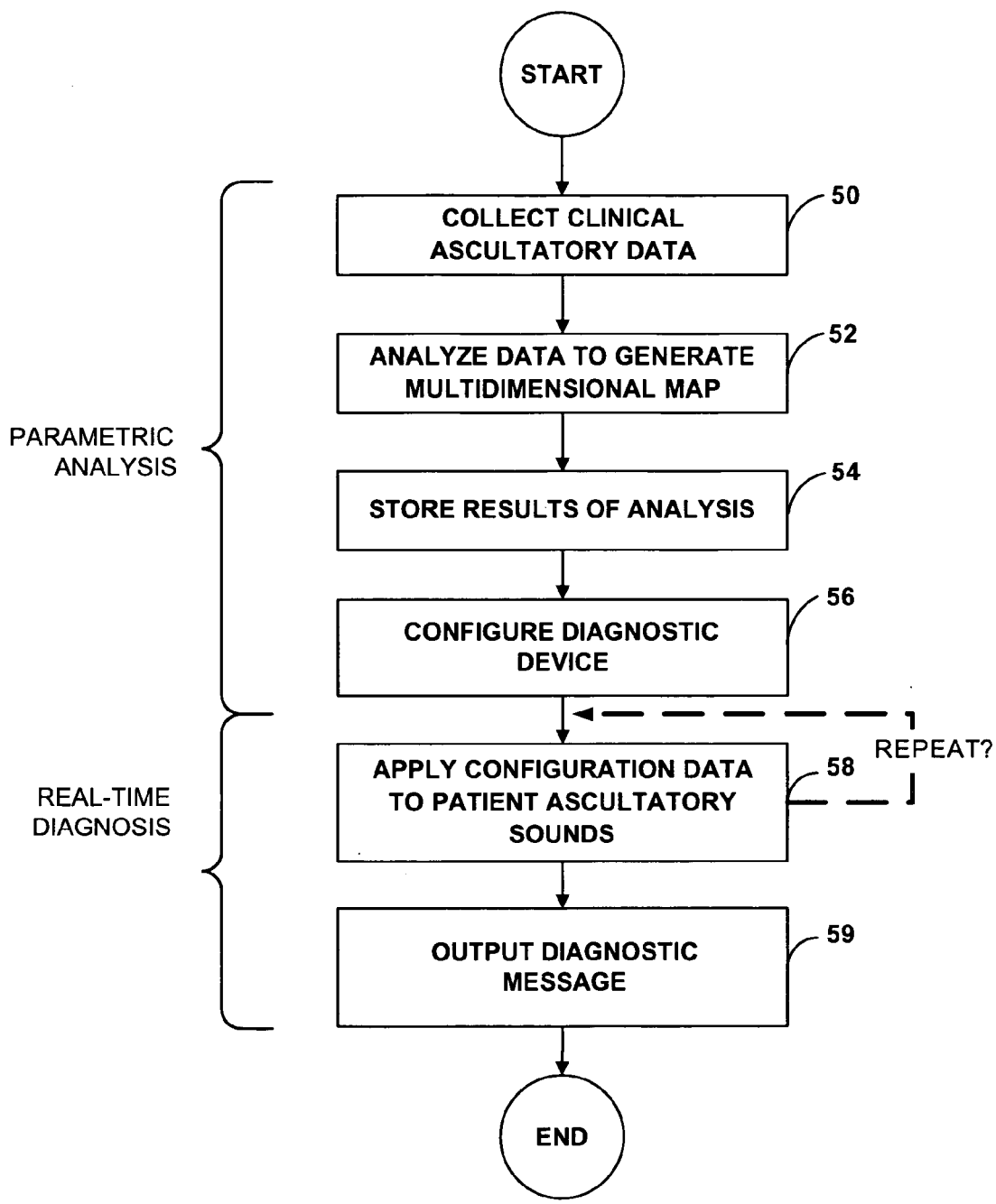
FIG. 4 is a flowchart that provides an overview of the techniques described herein.

FIG. 4 is a flowchart that provides an overview of the techniques described herein. As illustrated in FIG. 4, the process may generally be divided into two stages. The first stage is referred to as the parametric analysis stage in which clinical data 12 (FIG. 1) is analyzed using SVD to produce configuration data 13 for diagnostic device 6. This process may be computationally intensive. The second stage is referred to as the diagnosis stage in which diagnostic device 6 applies the results of the analysis stage to aid the diagnosis of a patient. For purposes of illustration, the flowchart of FIG. 4 is described in reference to FIG. 1.

Initially, clinical data 12 is collected (50) and provided to data analysis system 4 for singular value decomposition (52). As described above, clinical data 12 comprises electronic recordings of auscultatory sounds from a set of patients having known cardiac conditions.

Analysis module 14 of data analysis system 4 analyzes the recorded heart sounds of clinical data 12 in accordance with the techniques described herein to define a set of disease regions within a multi-dimensional space representative of the electronically recorded heart sounds (52). Each disease region within the multi-dimensional space corresponds to sounds within a heart cycle that have been mathematically identified as indicative of the respective disease. Analysis module 14 stores the results of the analysis within parametric database 16 (54). In particular, the results include configuration data 13 for use by diagnostic device 6 to map patient auscultatory sounds to the generated multidimensional space. Once analysis module 14 has processed clinical data 12, diagnostic device 6 receives or is otherwise programmed to apply configuration data 13 to assist the diagnosis of patient 18 (56). In this manner, data analysis system can be viewed as applying the techniques described herein, including SVD, to analyze a representative sample set of auscultatory sounds recorded from patients having know physiological conditions to generate parametric data that may be applied in real-time or pseudo real-time.

The diagnosis stage commences when auscultatory sound recording device 18 captures auscultatory sounds from patient 8. Diagnosis device 6 applies configuration data 13 to map the heart sounds received from auscultatory sound recording device 18 to the multi-dimensional energy space computed by data analysis system 4 from clinical data 12 (58). For cardiac auscultatory sounds, diagnostic device 6 may repeat the real-time diagnosis for one or more heart cycles identified with the recorded heart sounds of patient 8 to help ensure that an accurate diagnosis is reported to clinician 10. Diagnostic device 6 outputs a diagnostic message based on the application of the configuration and the mapping of the patient auscultatory sounds to the multidimensional space (59).

Figure 5:
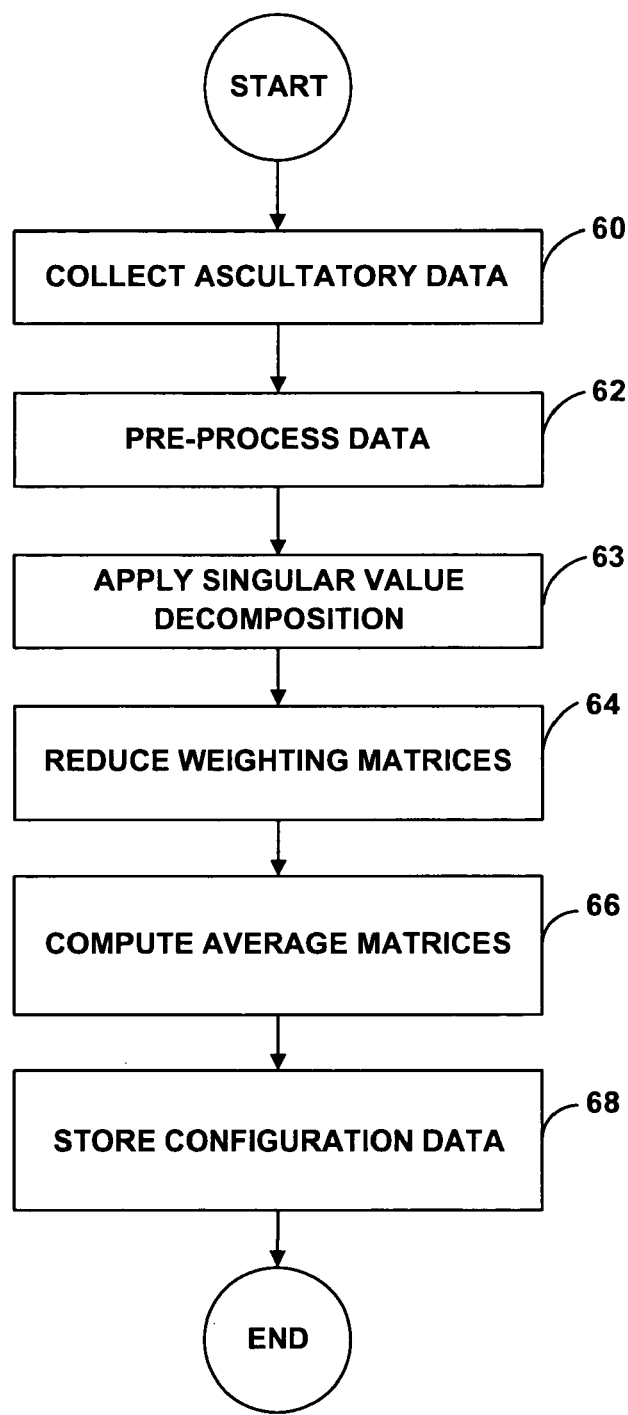
FIG. 5 is a flowchart illustrating a parametric analysis stage in which singular value decomposition is applied to clinical data.

FIG. 5 is a flowchart illustrating the parametric analysis stage (FIG. 4) in further detail. Initially, clinical data 12 is collected from a set of patients having known cardiac conditions (60). In one embodiment, each recording captures approximately eight seconds of auscultatory heart sounds, which represents approximately 9.33 heart cycles for a seventy beat per minute heart rate. Each recording is stored in digital form as a vector R having 32,000 discrete values, which represents a sampling rate of approximately 4000 Hz.

Each heart sound recording R is pre-processed (62), as described in detail below with reference to FIG. 6. During this pre-processing, analysis module 12 processes the vector R to identify a starting time and ending time for each heart cycle. In addition, analysis module 14 identifies starting and ending times for the systole and diastole periods as well as the S1 and S2 periods within each of the heart cycles. Based on these identifications, analysis module 14 normalizes each heart cycle to a common heart rate, e.g., 70 beats per minute. In other words, analysis module 14 may resample the digitized data corresponding to each heart cycle as necessary in order to stretch or compress the data associated with the heart cycle to a defined time period, such as approximately 857 ms, which corresponds to a heart rate of 70 beats per minute.

After pre-processing each individual heart recording, analysis module 14 applies singular value decomposition (SVD) to clinical data 12 to generate a multidimensional energy space and define disease regions within the multi-dimensional energy space that correlate to characteristics of the auscultatory sound (64).

More specifically, analysis module 14 combines N pre-processed sound recordings R for patients having the same known cardiac condition to form an N×M matrix A as follows:

$$A = \begin{bmatrix} 1 & \ldots & M \\ N & \ldots & M \end{bmatrix},$$

where each row represents a different sound recording R having M digitized values, e.g., 3400 values.

Next, analysis module 14 applies SVD to decompose A into the product of three sub-matrices:

$$A = UDV^T,$$

where U is an N×M matrix with orthogonal columns, D is an M×M non-negative diagonal matrix and V is an M×M orthogonal matrix. This relationship may also be expressed as:

$$U^T AV = \text{diag}(S) = \text{diag}(\sigma_1, \ldots, \sigma_p),$$

where the elements of matrix S ($\sigma_1, \ldots, \sigma_p$) are the singular values of A. In this SVD representation, U is the left singular matrix and V is the right singular matrix. Moreover, U can be viewed as an M×M weighting matrix that defines characteristics with each R that best define the matrix A. More specifically, according to SVD principles, the U matrix provides a weighting matrix that maps the matrix A to a defined region within an M dimensional space.

Analysis module 14 repeats this process for each cardiac condition. In other words, analysis module 14 utilizes sound recordings R for "normal" patients to compute a corresponding matrix $A_{NORMAL}$ and applies SVD to generate a $U_{NORMAL}$ matrix. Similarly, analysis module computes an A matrix and a corresponding U matrix for each pathology. For example, analysis module 14 may generate a $U_{AS}$, $U_{AR}$, a $U_{TR}$, and/or a $U_{DISEASED}$, where the subscript "AS" designates a U matrix generated from patient or population of patients known by other diagnostic tools to display aortic stenosis. The subscript "AR" designates aortic regurgitation and the subscript "TR" designated tricuspid regurgitation in analogous manner.

Next, analysis module 14 pair-wise multiplies each of the computed U matrices with the other U matrices, and performs SVD on the resultant matrices in order to identify which portions of the U matrices best characterize the characteristics that distinguish between the cardiac conditions. For example, assuming matrices of $U_{NORMAL}$, $U_{AS}$, and $U_{AR}$, analysis module computes the following matrices:

$$T1 = U_{NORMAL} * U_{AS},$$

$$T2 = U_{NORMAL} * U_{AR}, \text{ and}$$

$$T3 = U_{AS} * U_{AR}.$$

Analysis module 14 next applies SVD on each of the resultant matrices T1, T2 and T3, which again returns a set of sub-matrices that can be used to identify the portions of each original U matrix that maximizes energy differences within the multidimensional space between the respective cardiac conditions. For example, the matrices computed via applying SVD to T1 can be used to identify those portions of $U_{NORMAL}$ and $U_{AS}$ that maximize the orthogonality of the respective disease regions within the multidimensional space.

Consequently, T1 may be used to trim or otherwise reduce $U_{NORMAL}$ and $U_{AS}$ to sub-matrices that may be more efficiently applied during the diagnosis (64). For example, S matrices computed by application of SVD to each of T1, T2 and T3 may be used. An inverse cosine may be applied to each S matrix to compute an energy angle between the respective two cardiac conditions within the multidimensional space. This energy angle may then be used to identify which portions of each of the U matrices best account for the energy differences between the diseases reasons within the multidimensional space.

Next, analysis module 14 computes an average vector AV for each of the cardiac conditions (66). In particular, for each N×M A matrix formulated from cardiac data 12, analysis module 14 computes a 1×N average vector AV that stores the average digitized values computed from the N sound recordings R within the matrix A. For example, analysis module 14 may compute $AV_{AS}$, $AV_{AR}$, $AV_{TR}$, and/or $AV_{DISEASED}$ vectors.

Analysis module 14 stores the computed AV average vectors and the U matrices, or the reduced U matrices, in parametric database 16 for use as configuration data 13. For example, analysis module 14 may store $AV_{AS}$, $AV_{AR}$, $AV_{TR}$, $U_{NORMAL}$, $U_{AS}$, and $U_{AR}$, for use as configuration data 13 by diagnostic device 6 (68).

Figure 6:
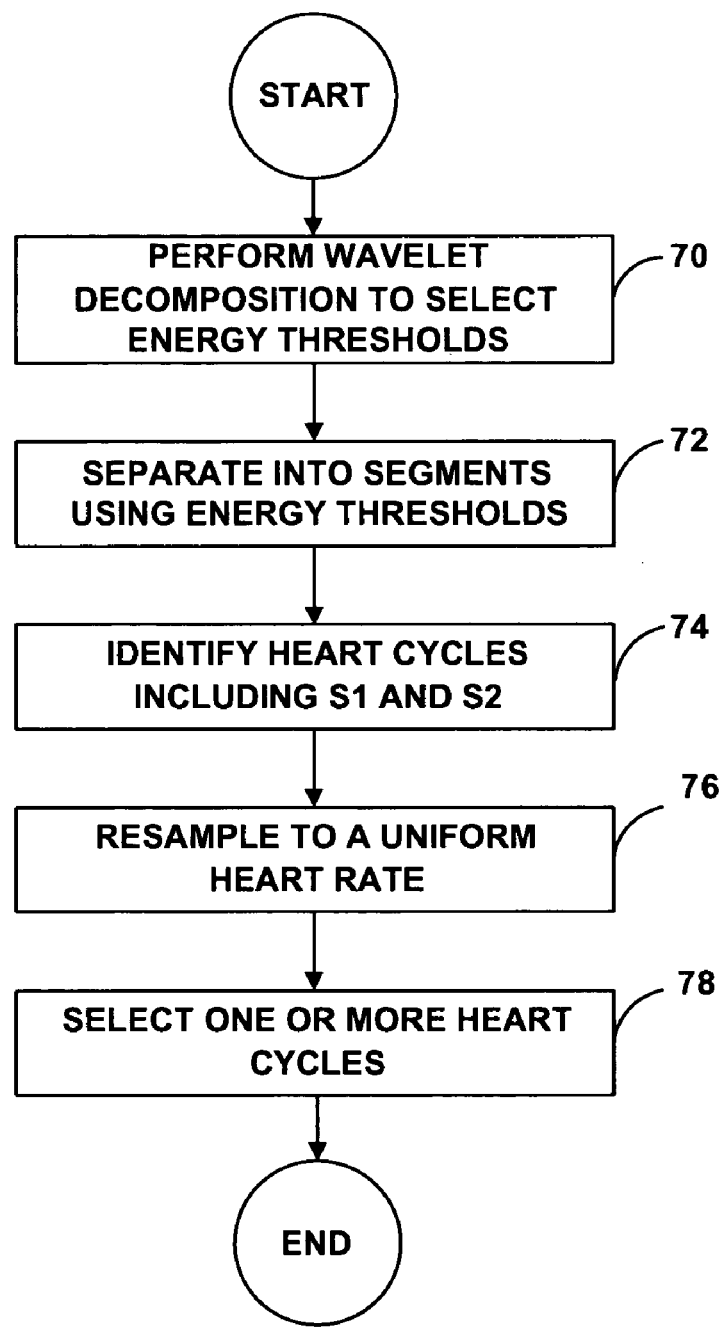
FIG. 6 is a flowchart that illustrates pre-processing of an auscultatory sound recording.

FIG. 6 is a flowchart that illustrates in further detail the pre-processing of an auscultatory sound recording R. In general, the pre-processing techniques separate the auscultatory sound recording R into heart cycles, and further separate each heart cycle into four parts: a first heart sound, a systole portion, a second heart sound, and a diastole portion. The pre-processing techniques apply Shannon Energy Envelogram (SEE) for noise suppression. The SEE is then thresholded making use of the relative consistency of the heart sound peaks. The threshold used can be adaptively generated based upon the specific auscultatory sound recording R.

Initially, analysis module 14 performs wavelet analysis on the auscultatory sound recording R to identify energy thresholds within the recording (70). For example, wavelet analysis may reveal energy thresholds between certain frequency ranges. In other words, certain frequency ranges may be identified that contain substantial portions of the energy of the digitized recording.

Based on the identified energy thresholds, analysis module 14 decomposes the auscultatory sound recording R into one or more frequency bands (72). Analysis module 14 analyzes the characteristics of the signal within each frequency band to identify each heart cycle. In particular, analysis module 14 examines the frequency bands to identify the systole and diastole stages of the heart cycle, and the S1 and S2 periods during with certain valvular activity occurs (74). To segment each heart cycle, analysis module 14 may first apply a low-pass filter, e.g., an eight order Chebyshev-type low-pass filter with a cutoff frequency of 1 kHz. The average SEE may then be calculated for every 0.02 second segment throughout the auscultatory sound recording R with 0.01 second segment overlap as follows:

$$E_S = -\frac{1}{N} \sum_{i=1}^{N} X_{norm}^2(i) \log X_{norm}^2(i)$$

where $X_{norm}$ is the low-pass filtered and normalized sample of the sound recording and N is the number of signal samples in the 0.02 second segment, e.g., N equals 200. The normalized average Shannon Energy versus the time axis may then be computed as:

$$P_S(t) = \frac{E_S(t) - M(E_S(t))}{S(E_S(t))}$$

where $M(E_S(t))$ is the mean of $E_S(t)$ and $S(E_S(t))$ is the standard deviation of $E_S(t)$. The mean and standard deviation are then used as a basis for identifying the peaks with each heart cycle and the starting and times for each segment with each heart cycle.

Once the starting and ending times for each heart cycle and each S1 and S2 periods is determined within the auscultatory sound recording R, analysis module 14 re-samples the auscultatory sound recording R as necessary to stretch or compress so that each heart cycle and each S1 and S2 period occur over a time period (76). For example, analysis module 14 may normalize each heart cycle to a common heart rate, e.g., 70 beats per minute and may ensure that each S1 and S2 period within the cycle correspond to an equal length in time. This may advantageously allow the portions of the auscultatory sound recording R for the various phases of the cardiac activity to be more easily and accurately analyzed and compared with similar portions of the other auscultatory sound recordings.

Upon normalizing the heart cycles within the digitized sound recording R, analysis module 14 selects one or more of the heart cycles for analysis (78). For example, analysis module 14 may identify a "cleanest" one of the heart cycles based on the amount of noise present within the heart cycles. As other examples, analysis module 14 may compute an average of all of the heart cycles or an average to two or more randomly selected heart cycles for analysis.

Figure 7:
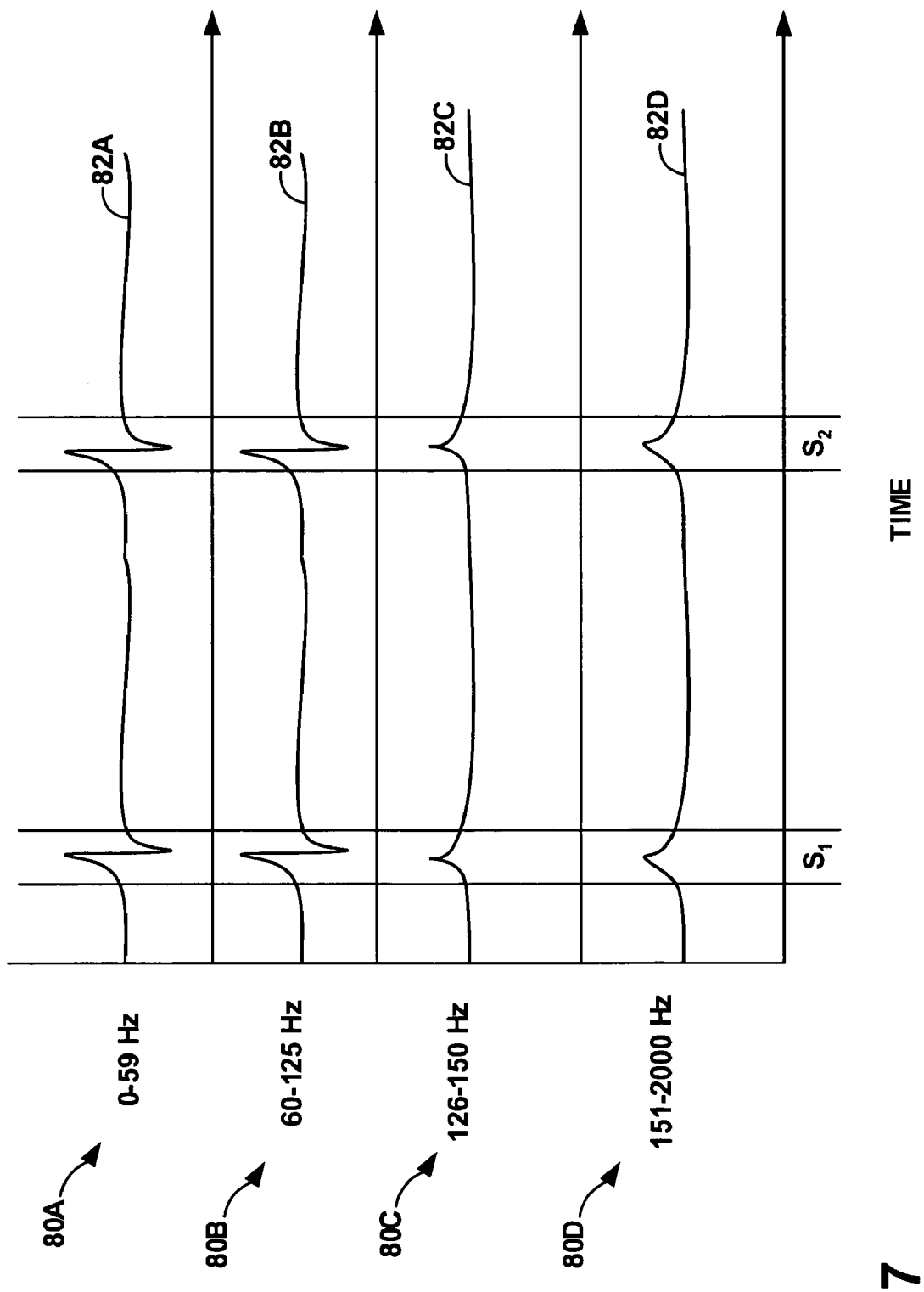
FIG. 7 is a graph that illustrates an example result of wavelet analysis and energy thresholding while pre-processing the auscultatory sound recording.

FIG. 7 is a graph that illustrates an example result of the wavelet analysis and energy thresholding described above in reference to FIG. 6. In particular, FIG. 7 illustrates a portion of a sound recording R. In this example, analysis module 14 has decomposes an exemplary auscultatory sound recording R into four frequency bands 80A-80D, and each frequency band includes a respective frequency component 82A-82D.

Based on the decomposition, analysis module 14 detects changes to the auscultatory sounds indicative of the stages of the heart cycle. By analyzing the decomposed frequencies and identifying the relevant characteristics, e.g., changes of slope within one or more of the frequency bands 80, analysis module 14 is able to reliably detect the systole and diastole periods and, in particular, the start and end to the S1 and S2 periods.

Figure 8:
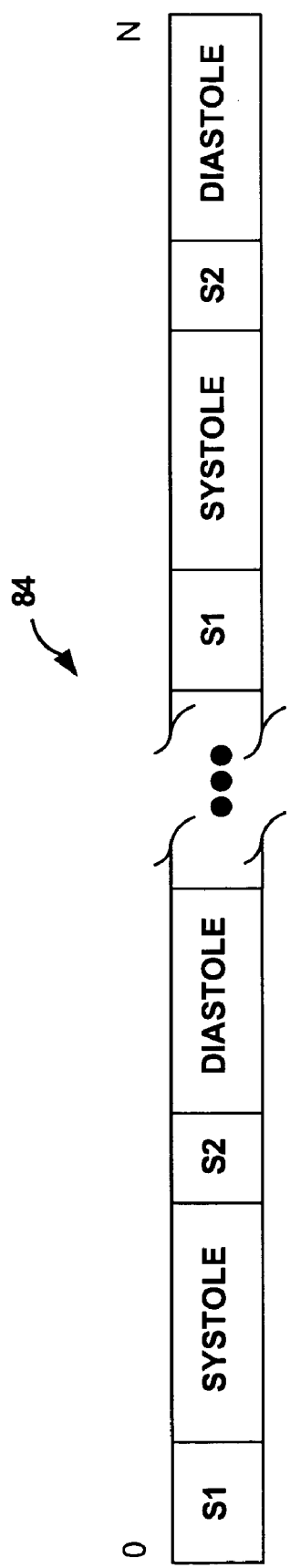
FIG. 8 illustrates an example data structure of an auscultatory sound recording.

FIG. 8 illustrates an example data structure 84 of an auscultatory sound recording R. As illustrated, data structure 84 may comprise a 1×N vector storing digitized data representative of the auscultatory sound recording R. Moreover, based on the pre-processing and re-sampling, data structure 84 stores data over a fixed number of heart cycles, and each S1 and S2 region occupy a pre-defined portion of the data structure. For example, S1 region 86 for the first heart cycle may comprise elements 0-399 of data structure 84, and systole region 87 of the first heart cycle may comprises elements 400-1299. This allows multiple auscultatory sound recordings R to be readily combined to form an N×M matrix A, as described above, in which the S1 and S2 regions for a given heart cycle are column-aligned.

Figure 9:
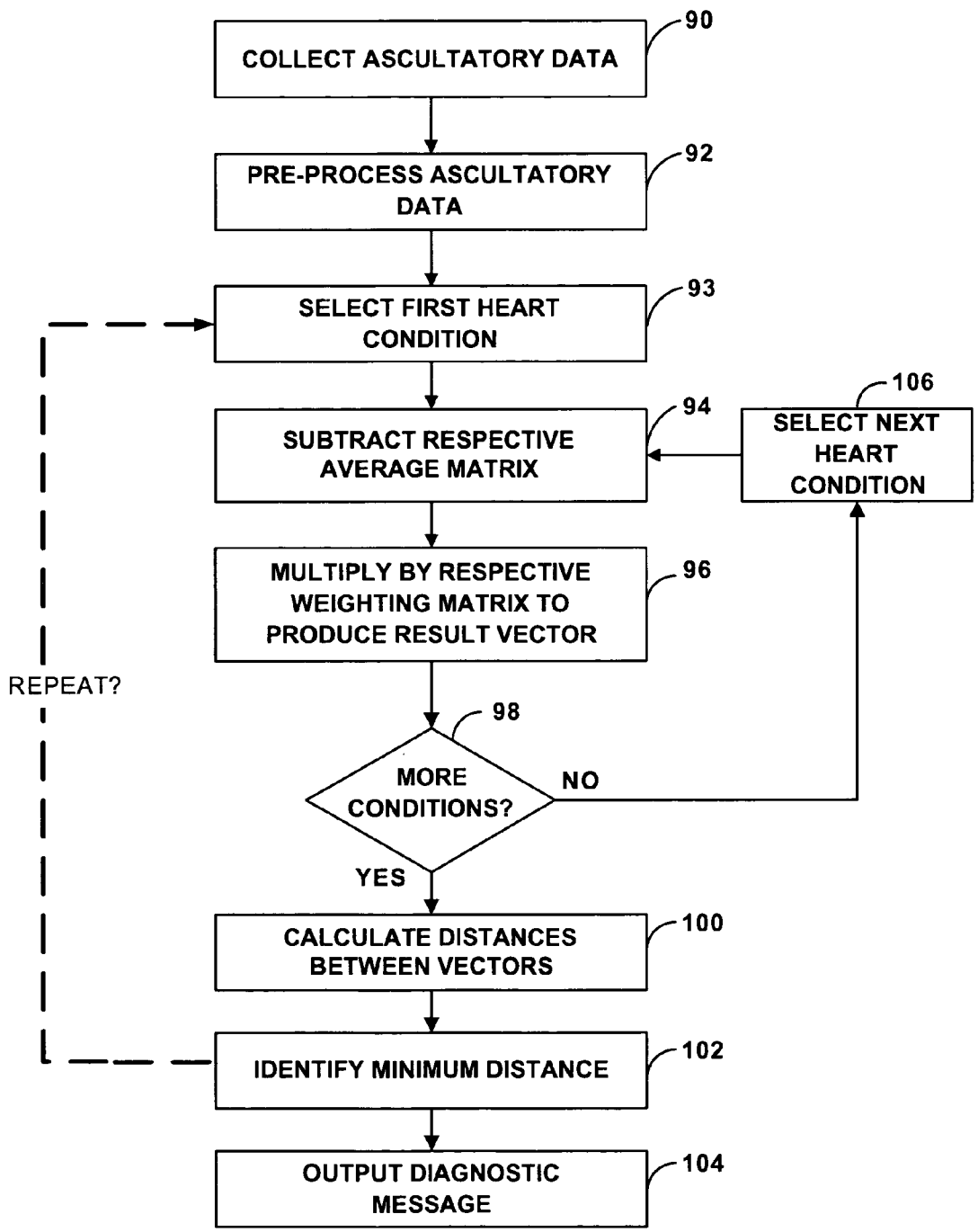
FIG. 9 is a flowchart illustrating a real-time diagnostic stage in which a diagnostic device applies configuration data from the parametric analysis stage to provide a recommended diagnosis for a digitized representation of auscultatory sounds of a patient.

FIG. 9 is a flowchart illustrating the diagnostic stage (FIG. 4) in further detail. Initially, auscultatory data is collected from patient 8 (90). As described above, the auscultatory data may be collected by a separate auscultatory sound recording device 18, e.g., an electronic stethoscope, and communicated to diagnostic device 6 via link communication 19. In another embodiment, the functionality of diagnostic device 6 may be integrated within auscultatory sound recording device 18. Similar to the parametric analysis stage, the collected auscultatory recording captures approximately eight seconds of auscultatory sounds from patient 8, and may be stored in digital form as a vector $R_{PAT}$ having 3400 discrete values.

Upon capturing the auscultatory data $R_{PAT}$, diagnostic device 6 pre-processes the heart sound recording $R_{PAT}$ (92), as described in detail above with reference to FIG. 6. During this pre-processing, diagnostic device 6 processes the vector $R_{PAT}$ to identify a starting time and an ending time for each heart cycle, and starting and ending times for the systole and diastole periods as well as the S1 and S2 periods of each of the heart cycles. Based on these identifications, diagnostic device 6 normalizes each heart cycle to a common heart rate, e.g., 70 beats per minute.

Next, diagnostic device 6 initializes a loop that applies configuration data 13 for each physiological condition examined during the analysis stage. For example, diagnostic device may utilize configuration data of $AV_{AS}$, $AV_{AR}$, $AV_{TR}$, $U_{NORMAL}$, $U_{AS}$, and $U_{AR}$, to assist diagnosis of patient 8.

Initially, diagnostic device 6 selects a first physiological condition, e.g., normal (93). Diagnostic device 6 then subtracts the corresponding average vector AV from the captured auscultatory sound vector $R_{PAT}$ to generate a difference vector D (94). D is referred to generally as a difference vector as the resulting digitized data of D represents differences between the captured heart sound vector $R_{PAT}$ and the currently selected physiological condition. For example, diagnostic device 6 may calculate $D_{NORMAL}$ as follows:

$$D_{NORMAL} = R_{PAT} - AV_{NORMAL}.$$

Diagnostic device 6 then multiples the resulting difference vector D by the corresponding U matrix for the currently selected physiological condition to produce a vector P representative of patient 8 with respect to the currently selected cardiac condition (96). For example, diagnostic device 6 may calculate $P_{NORMAL}$ vector as follows:

$$P_{NORMAL} = D_{NORMAL} * U_{NORMAL}.$$

Multiplying the difference vector D via the corresponding U matrix effectively applies a weighting matrix associated with the corresponding disease region within the multi-dimensional space, and produces a vector P within the multidimensional space. The alignment of the vector P relative to the disease region of the current cardiac condition depends on the normality of the resulting difference vector D and the U matrix determined during the analysis stage.

Diagnostic device 6 repeats this process for each cardiac condition defined within the multidimensional space to produce a set of vectors representative of the auscultatory sound recorded from patient 8 (98, 106). For example, assuming configuration data 13 comprises $AV_{AS}$, $AV_{AR}$, $AV_{TR}$, $U_{NORMAL}$, $U_{AS}$, and $U_{AR}$, diagnostic device 6 calculates four patient vectors as follows:

$$P_{NORMAL} = D_{NORMAL} * U_{NORMAL},$$

$$P_{AS} = D_{AS} * U_{AS},$$

$$P_{AR} = D_{AR} * U_{AR}, \text{ and}$$

$$P_{TR} = D_{TR} * U_{TR}.$$

This set of vectors represents the auscultatory sounds recorded from patient 8 within the multidimensional space generated during the analysis stage. Consequently, the distance between each vector and the corresponding disease region represents a measure of similarity between the characteristics of the auscultatory sounds from patient 8 and the characteristics of auscultatory sounds of patients known to have the respective cardiac conditions.

Diagnostic device 6 then selects one of the disease regions as a function of the orientation of the vectors and the disease regions within the multidimensional space. In one embodiment, diagnostic device determines which of the disease regions defined within the energy space has a minimum distance from the representative vectors. For example, diagnostic device 6 first calculates energy angles representative of the minimum angular distances between each of the vectors P and the defined disease regions (100). Continuing with the above example, diagnostic device 6 may compute the following four distance measurements:

$$DIST_{NORMAL} = P_{NORMAL} - \text{MIN}[P_{AS}, P_{AR}, P_{TR}],$$

$$DIST_{AS} = P_{AS} - \text{MIN}[P_{NORMAL}, P_{AR}, P_{TR}],$$

$$DIST_{AR} = P_{AR} - \text{MIN}[P_{AS}, P_{NORMAL}, P_{TR}], \text{ and}$$

$$DIST_{TR} = P_{TR} - \text{MIN}[P_{AS}, P_{AR}, P_{NORMAL}].$$

In particular, each distance measurement DIST is a two-dimensional distance between the respective patient vector P and the mean of each of the defined disease regions within the multidimensional space.

Based on the computed distances, diagnostic device 6 identifies the smallest distance measurement (102) and determines a suggested diagnosis for patient 8 to assist clinician 10. For example, if of the set of patient vectors $P_{AS}$ is the minimum distance away from its respective disease space, i.e., the AS disease space, diagnostic device 6 determines that patient 8 may likely be experiencing aortic stenosis. Diagnostic device 6 outputs a representative diagnostic message to clinician 10 based on the identification (104). Prior to outputting the message, diagnostic device 6 may repeat the analysis for one or more heart cycles identified with the recorded heart sounds of patient 8 to help ensure that an accurate diagnosis is reported to clinician 10.

EXAMPLES

The techniques described herein were applied to clinical data for a set of patients known to either "normal" cardiac activity or aortic stenosis. In particular, a multidimensional space was generated based on the example clinical data, and then the patients were assessed in real-time according to the techniques described herein.

The following table shows distance calculations for the auscultatory sounds for the patients known to have normal cardiac conditions. In particular, vectors were computed for each of the measured heart cycles for each patient. Table 1 shows distances for the vectors, measured in volts, with respect to a disease region within the multidimensional space associated with the normal cardiac condition.

TABLE 1

| HEART CYCLE | PATIENT 1 | PATIENT 2 | PATIENT 3 |
|---|---|---|---|
| 1 | 0.45 | 0.25 | 0.20 |
| 2 | 0.64 | 0.14 | 0.18 |
| 3 | 0.38 | 0.21 | 0.32 |
| 4 |  | 0.36 |  |
| 5 |  | 0.20 |  |
| 6 |  | 0.33 |  |

Table 2 shows distance calculations, measured in volts, for the auscultatory sounds for the patients known to have aortic stenosis. In particular, Table 2 shows energy distances for the vectors with respect to a region within the multidimensional space associated with the aortic stenosis cardiac condition.

TABLE 2

| HEART CYCLE | PATIENT 4 | PATIENT 5 |
|---|---|---|
| 1 | −0.43 | −0.49 |
| 2 | −0.67 | −0.43 |
| 3 | −0.55 | −0.37 |
| 4 | −0.43 | −0.64 |
| 5 | −0.34 | −0.17 |
| 6 | −0.44 | −0.14 |
|  | −0.60 |  |

As illustrated by Table 1 and Table 2, the vectors are clearly separate within the multidimensional space, an indication that diagnosis can readily be made. All five patients followed a similar pattern.

Figure 10A:
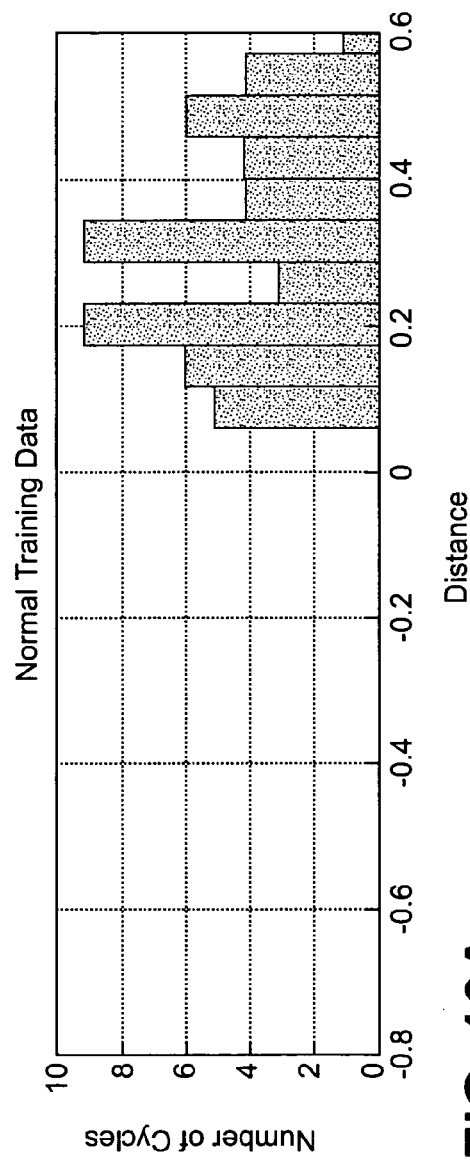
FIGS. 10A and 10B are graphs that illustrate exemplary results of the techniques by comparing aortic stenosis data to normal data.
Figure 10B:
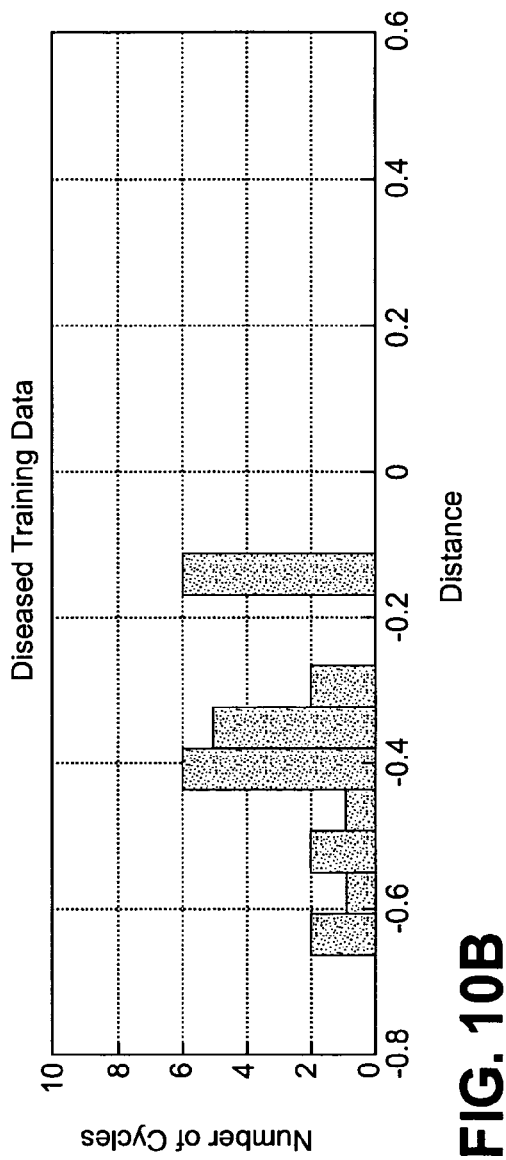
Figure 11A:
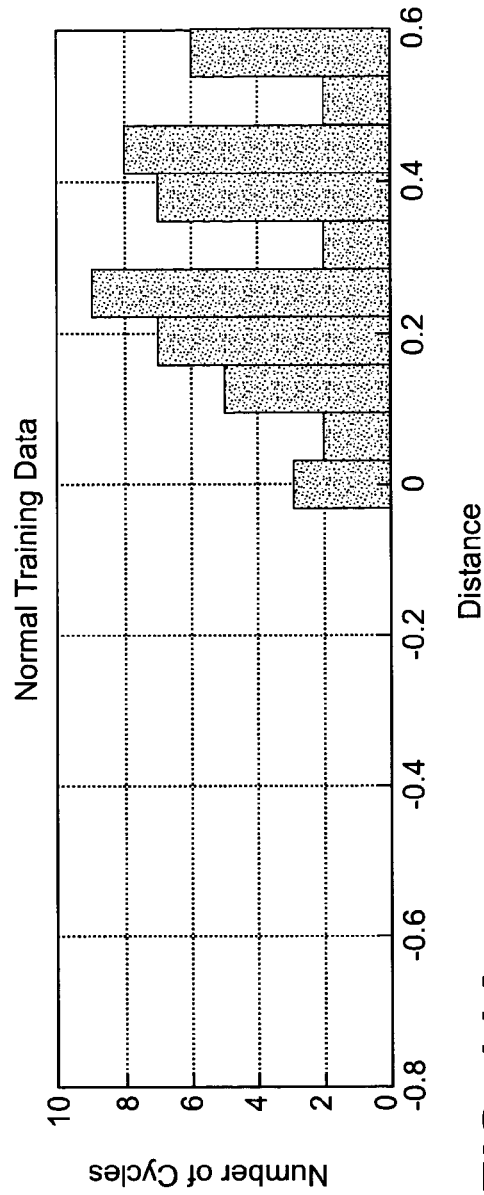
FIGS. 11A and 11B are graphs that illustrate exemplary results of the techniques by comparing tricuspid regurgitation data to normal data.
Figure 11B:
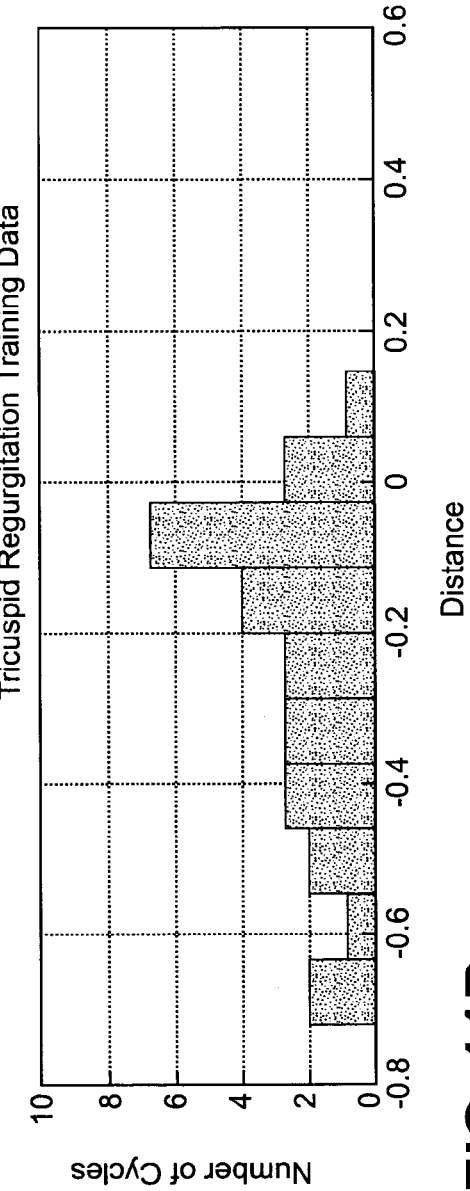
Figure 12A:
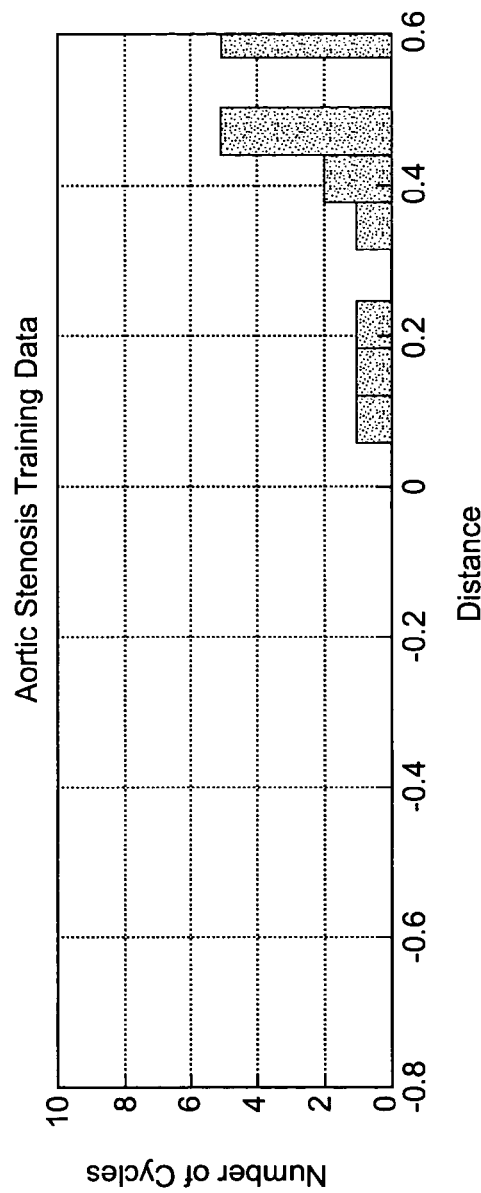
FIGS. 12A and 12B are graphs that illustrate exemplary results of the techniques by comparing aortic stenosis data to tricuspid regurgitation data.
Figure 12B:
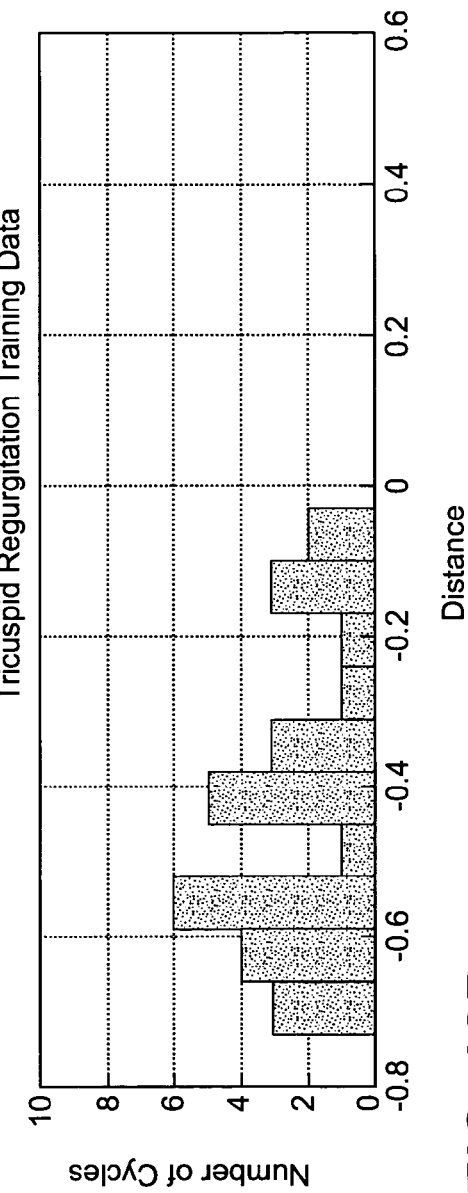

FIGS. 10A and 10B are graphs that generally illustrate the exemplary results. In particular, FIGS. 10A and 10B illustrate aortic stenosis data compared to normal data. Similarly, FIGS. 11A and 11B are graphs that illustrate tricuspid regurgitation data compared to normal data. FIGS. 12A and 12B are graphs that illustrate aortic stenosis data compared to tricuspid regurgitation data. In general, the graphs of FIGS. 10A, 10B, 11A, and 11B illustrate that the techniques result in substantially non-overlapping data for the normal data and disease-related data.

Various embodiments of the invention have been described. For example, although described in reference to sound recordings, the techniques may be applicable to other electrical recordings from a patient. The techniques may be applied, for example, to electrodiagram recordings electrically sensed from a patient. These and other embodiments are within the scope of the following claims.

The invention claimed is:

1. A method comprising:
   mapping auscultatory sounds associated with known physiological conditions to a set of one or more disease regions defined within a multidimensional space by:
   (i) formulating a set of matrices that store digitized representations of the auscultatory sounds associated with the known physiological conditions, wherein each matrix is associated with a different one of the physiological conditions and stores the digitized representations of the auscultatory sounds associated with the respective physiological condition, and
   (ii) applying singular value decomposition ("SVD") to each of the matrices to compute respective sets of sub-matrices that define the disease regions within the multidimensional space;
   programming a diagnostic device in accordance with configuration data generated by the application of SVD to the set of matrices, wherein the configuration data includes at least one of the sub-matrices associated with the different physiological conditions;

generating, with the diagnostic device, a set of one or more vectors within the multidimensional space representative of auscultatory sounds associated with a patient; and outputting, with the diagnostic device, a diagnostic message associated with a physiological condition of the patient as a function of the vectors and the disease regions defined within the multidimensional space.

2. The method of claim 1, wherein outputting a diagnostic message comprises;
selecting one of the disease regions of the multidimensional space as a function of orientations of the vectors within the multidimensional space; and
outputting the diagnostic message based on the selection.

3. The method of claim 2, wherein each of the vectors correspond to a respective one of the disease regions, and wherein selecting one of the disease regions comprises selecting one of the disease regions as a function of a distance between each of the vectors and the respective disease region.

4. The method of claim 3, wherein selecting one of the disease regions comprises:
identifying which of the vectors has a minimum distance from its respective disease region; and
selecting the disease region associate with the identified vectors.

5. The method of claim 1, wherein each disease region within the multi-dimensional space is defined by characteristics of the auscultatory sounds associated with the known physiological conditions that have been identified as indicators for the respective physiological condition.

6. The method of claim 1, wherein outputting a diagnostic message comprises outputting a diagnostic message identifying one or more specific pathologies currently being experienced by patient.

7. The method of claim 1, wherein outputting a diagnostic message comprises outputting the diagnostic message to indicate the patient is susceptible to one or more of the physiological conditions.

8. The method of claim 1, wherein each of the matrices comprises an N×M matrix storing N of the digitized representations and M digital values for each of the digitized representations.

9. The method of claim 1, wherein formulating a set of matrices comprises formulating the set of matrices to store digitized representations in a raw format that has not been filtered.

10. The method of claim 1, further comprising storing at least a portion of one or more of the sub-matrices within a database for use as configuration data for a diagnostic device.

11. The method of claim 10, further comprising storing the configuration data in a format that can be used by the diagnostic device to compute the vectors to represent the auscultatory sounds associated with the patient within the multidimensional space.

12. The method of claim 10, further comprising:
computing respective average vectors from the set of matrices, wherein each average vector represents an average of the digitized representations of the auscultatory sounds associated with the respective physiological conditions; and
applying the average vectors and the configuration data with the diagnostic device to the auscultatory sounds associated with the patient to generate the set of vectors within the multidimensional space.

13. The method of claim 12, wherein applying the average vectors and the configuration data with the diagnostic device comprises:
subtracting the corresponding average vectors from a vector representing the auscultatory sounds associated with the patient to generate a set of difference vectors, wherein each difference vector corresponds to a different one of the disease regions in the multi-dimensional space; and
applying the sub-matrices of the configuration data to the difference vectors to generate the vectors representative of the auscultatory sounds associated with the patient.

14. The method of claim 13, wherein applying the sub-matrices of the configuration data comprises multiplying the difference vectors by the corresponding one of the U sub-matrices to produce a respective one of the vectors representative of the auscultatory sounds associated with the patient.

15. The method of claim 1, wherein applying SVD comprises applying SVD to decompose a matrix A of the set of matrices into the product of three sub-matrices as:

$$A = UDV^T,$$

where U is an N×M matrix with orthogonal columns, D is an M×M non-negative diagonal matrix and V is an M×M orthogonal matrix.

16. The method of claim 15, further comprising:
computing a set of matrices Thy pair-wise multiplying each of the computed U matrices with tie other U matrices;
performing SVD on each of the resultant matrices T to decompose each matrix T into a respective set of sub-matrices; and
applying the sub-matrices generated from each of the matrices T to identify portions of the U matrices to be used in diagnosis of the patient.

17. The method of claim 16, wherein applying the sub-matrices generated from each of the matrices T comprises applying the sub-matrices generated from each of the matrices T to identify portions of the U matrices that maximize the orthogonality of the respective disease regions within the multidimensional space.

18. The method of claim 1, wherein each of the auscultatory sounds associated with known physiological conditions comprises a digitized representation of sounds recorded over a plurality of heart cycles.

19. The method of claim 1, wherein the physiological conditions include one or more of a normal physiological condition, aortic regurgitation, aortic stenosis, tricuspid regurgitation, tricuspid stenosis, pulmonary stenosis, pulmonary regurgitation, mitrial regurgitation, aortic aneurisms, carotid artery stenosis and mitrial stenosis.

20. The method of claim 1, further comprising:
capturing the auscultatory sounds associated with the patient using a first device; communicating a digitized representation of the captured auscultatory sounds from the first device to a second device;
analyzing the digitized representation with the second device to generate the set of vectors; and
outputting the diagnostic message with the second device.

21. The method of claim 20, wherein the first device comprises an electronic stethoscope.

22. The method of claim 20, wherein the second device comprises one of a mobile computing device, a personal digital assistant, and an echocardiogram analyzer.

23. The method of claim 1, wherein the diagnostic device is an electronic stethoscope, the method further comprising;
capturing the auscultatory sounds associated with the patient using an the electronic stethoscope;
analyzing the digitized representation with the electronic stethoscope to generate the set of vectors; and
outputting the diagnostic message to a display of the electronic stethoscope.

24. The method of claim 1, wherein the physiological conditions comprise cardiac conditions and the auscultatory sounds associated with the patient comprises heart sounds.

25. The method of claim 1, wherein the auscultatory sounds associated with the patient comprises lungs sounds.

26. A method comprising:
mapping auscultatory sounds associated with known physiological conditions to a set of one or more disease regions defined within multidimensional space;
generating a set of one or more vectors within the multidimensional space representative of auscultatory sounds associated with a patient; and
outputting a pass/fail message that indicates whether an abnormal physiological condition of the patient has been detected as a function of the vectors and the disease regions defined within the multidimensional space.

27. A method comprising:
mapping auscultatory sounds associated with known physiological conditions to a set of one or more disease regions defined within a multidimensional space;
generating a set of one or more vectors within the multidimensional space representative of auscultatory sounds associated with a patient; and
outputting a diagnostic message associated with a physiological condition of the patient as a function of the vectors and the disease regions defined within the multidimensional space, wherein outputting a diagnostic message comprises selecting a message type for the diagnostic message based on a user configurable mode.

28. The method of claim 27, wherein the message type comprises one of a pass/fail message type, a suggested diagnosis message type, and a predictive diagnosis message type.

29. A method comprising:
mapping auscultatory sounds associated with known physiological conditions to a set of one or mare disease regions defined within a multidimensional space;
generating a set of one or more vectors within the multidimensional space representative of auscultatory sounds associated with a patient; and
outputting a diagnostic message associated with a physiological condition of the patient as a function of the vectors and the disease regions defined within the multidimensional space,
wherein the diagnostic message comprises a severity indicator based on a calculated distance from at least one of the vectors and a normal region within the multidimensional space.

30. A method comprising:
mapping auscultatory sounds associated with known physiological conditions to a set of one or more disease regions defined within a multidimensional space, wherein each of the auscultatory sounds associated with known physiological conditions comprises a digitized representation of sounds recorded over a plurality of heart cycles, and wherein mapping auscultatory sounds comprises:

(i) processing each of the digitized representations to identify a starting point and ending point for each of the heart cycles;
(ii) processing each of the digitized representations to identify starting and ending times for systole and diastole periods of each of the heart cycles, and S1 and S2 periods for each of the heart cycles; and
(iii) re-sampling the digitized representations based on the identified starting and ending times for the systole and diastole periods and the S1 and S2 periods to normalize each of the heart cycles to a common heart rate;
generating a set of one or more vectors within the multidimensional space representative of auscultatory sounds associated with a patient; and
outputting a diagnostic message associated with a physiological condition of the patient as a function of the vectors and the disease regions defined within the multidimensional space.

31. A method comprising:
formulating a set of matrices that store digitized representations of auscultatory sounds associated with the physiological conditions, wherein each matrix is associated with a different one of the physiological conditions and stores the digitized representations of the auscultatory sounds associated with the respective physiological condition;
applying singular value decomposition ("SVD") to each of the matrices to decompose the matrices into respective sets of sub-matrices that define disease regions within the multidimensional space; and
computing respective average vectors from the set of matrices, wherein each average vector represents an average of the digitized representations of the auscultatory sounds associated with the respective physiological conditions;
generating configuration data to include the average vectors; and
outputting the configuration data for application by a diagnostic device based on the multidimensional mapping.

32. The method of claim 31, wherein outputting configuration data comprises storing at least a portion of one or more of the sub-matrices for each of the physiological conditions within a database.

33. The method of claim 31, wherein applying SVD comprises applying SVD to decompose a matrix A of the set of matrices into the product of three sub-matrices as:

$A=UDV^T$, where U is an N×M matrix with orthogonal columns, D is an M×M non-negative diagonal matrix and V is an M×M orthogonal matrix.

34. The method of claim 33, further comprising:
computing a set of matrices T by pair-wise multiplying each of the computed U matrices with the other U matrices;
performing SVD on each of the resultant matrices T to decompose each matrix T into a respective set of sub-matrices; and
applying the sub-matrices generated from each of the matrices T to identify portions of the U matrices to be used in diagnosis of the patient.

35. The method of claim 34, wherein applying the sub-matrices generated from each of the matrices T comprises applying the sub-matrices generated from each of the matrices T to identify portions of the U matrices that maximize the orthogonality of the respective disease regions within the multidimensional space.

36. The method of claim 31, wherein the physiological conditions include one or more of a normal physiological condition, aortic regurgitation, aortic stenosis, tricuspid regurgitation, tricuspid stenosis, pulmonary stenosis, pulmonary regurgitation, mitrial regurgitation, aortic aneurisms, carotid artery stenosis and mitrial stenosis.

37. A method comprising:
storing within a diagnostic device configuration data generated by the application of singular value decomposition ("SVD") to digitized representations of electrical recordings associated with physiological conditions, wherein the configuration data maps the electrical recordings to a set of one or more disease regions within a multidimensional space;
applying the configuration data to a digitized representation of an electrical recording associated with a patient to generate a set of one or more vectors within the multidimensional space;
selecting one of the physiological conditions based on the vectors; and
outputting a pass/fail diagnostic message indicating the selected one of the physiological conditions.

38. The method of claim 37,
wherein selecting one the physiological conditions comprises selecting one of the disease regions of the multidimensional space as a function of orientations of the vectors within the multidimensional space; and
wherein outputting the diagnostic message comprises outputting the diagnostic message based on the selection.

39. The method of claim 38, wherein each of the vectors correspond to a respective one of the disease regions, and wherein selecting one of the disease regions comprises selecting one of the disease regions as a function of a distance between each of the vectors and the respective disease region.

40. The method of claim 37, wherein the configuration data comprises a sub-matrix generated by the application of SVD to the digitized representations of the auscultatory sounds associated with the known physiological conditions.

41. The method of claim 37, wherein the electrical recordings comprises echocardiogram.

42. The method of claim 37, wherein the electrical recordings comprises digitized representation of auscultatory sounds.

43. The diagnostic device of claim 37, wherein the diagnostic device comprises one of a mobile computing device, a personal digital assistant, an echocardiogram analyzer, and an electronic stethoscope.

44. A diagnostic device comprising:
a medium that stores data generated by the application of singular value decomposition ("SVD") to digitized representations of auscultatory sounds associated with known physiological conditions, wherein the data maps the auscultatory sounds to a set of one or more disease regions within a multidimensional space; and
a control unit that applies the configuration data to a digitized representation representative of auscultatory sounds associated with a patient to generate a set of one or more vectors within the multidimensional space and select one of the physiological conditions based on the vectors, wherein the control unit outputs a pass/fail diagnostic message indicating the selected one of the physiological conditions.

45. The diagnostic device of claim 44,
wherein the control unit selects one of the physiological conditions based on orientations of the vectors relative to the disease regions within the multidimensional space.

46. The diagnostic device of claim 45, wherein each of the vectors correspond to a respective one of the disease regions, and wherein the control unit selects one of the disease regions as a function of a distance between each of the vectors and the respective disease region.

47. The diagnostic device of claim 45, wherein the configuration data comprises a sub-matrix generated by the application of SVD to the digitized representations of the auscultatory sounds associated with the known physiological conditions.

48. A data analysis system comprising:
an analysis module to map the auscultatory sounds to a set of one or more disease regions within a multidimensional space, wherein the analysis module generates data mapping the auscultatory sounds by: (i) formulating a set of matrices that store digitized representations of the auscultatory sounds associated with the known physiological conditions wherein the matrices are associated with different physiological conditions and store the digitized representations of the auscultatory sounds associated with the respective physiological condition, and (ii) applying singular value decomposition ("SVD") to the matrices to compute respective sets of sub-matrices that define the disease regions within the multidimensional space;
a database to store the data generated by the analysis module; and
a diagnostic device programmed in accordance with the data generated by the analysis module, wherein the data includes at least one of the sub-matrices associated with the different physiological conditions, and wherein the diagnostic device generates a set of one or more vectors within the multidimensional space representative of auscultatory sounds associated with a patient and outputs a diagnostic message associated with one of the physiological conditions of the patient as a function of the vectors and the disease regions defined within the multidimensional space.

49. The system of claim 48, wherein the electrical recordings comprises echocardiogram.

50. The system of claim 48, wherein the electrical recordings comprises digitized representation of auscultatory sounds.

51. The data analysis system of claim 48,
wherein the analysis module formulates a set of matrices that store the digitized representations of the auscultatory sounds associated with the physiological conditions, wherein each matrix is associated with a different one of the physiological conditions and stores the digitized representations of the auscultatory sounds associated with the respective physiological condition, and
wherein the analysis module applies SVD to each of the matrices to decompose the matrices into respective sets of sub-matrices that define the disease regions within the multidimensional space, and
wherein the analysis module stores within the database at least one of the sub-matrices for each of the disease regions.

52. A computer-readable medium comprising instructions that cause a processor to:

apply configuration data to a digitized representation representative of auscultatory sounds associated with a patient to generate a set of one or more vectors within a multidimensional space representative of auscultatory sounds to select one of a set of physiological conditions, wherein the configuration maps the auscultatory sounds to a set of one or more disease regions within the multidimensional space; and output a pass/fail diagnostic message indicating the selected one of the physiological conditions.

53. The computer-readable medium of claim 52 further comprising instructions to cause the processor to:

apply the configuration data to the digitized representation representative of the auscultatory sounds associated with the patient to generate a set of one or more vectors within the multidimensional space;

select one of the disease regions of the multidimensional space as a function of orientations of the vectors relative to the disease regions within the multidimensional space; and output the diagnostic message based on the selection.

* * * * *

UNITED STATES PATENT AND TRADEMARK OFFICE
CERTIFICATE OF CORRECTION

PATENT NO. : 7,300,405 B2
APPLICATION NO. : 10/781118
DATED : November 27, 2007
INVENTOR(S) : Marie A. Guion et al.

It is certified that error appears in the above-identified patent and that said Letters Patent is hereby corrected as shown below:

Front page under ABSTRACT, "associated known physiological" should be --associated with known physiological--

Page 2 under OTHER PUBLICATIONS, Reference 1 "Critical Reviews in Bomedical" should be --Critical Reviews in Biomedical--

Page 2 under OTHER PUBLICATIONS, Reference 10, "IEE Colloquim on Signal" should be --IEEE Colloquium on Signal--

Page 2 under OTHER PUBLICATIONS, Reference 16, "Instrumentaiton" should be --Instrumentation--

Page 2 under OTHER PUBLICATIONS, Reference 28, "Dectection" should be --Detection--

Page 3 under OTHER PUBLICATIONS, Reference 2, "The Practioner" should be --The Practitioner--

Page 3 under OTHER PUBLICATIONS, Reference 4, "Cricial Reviews" should be --Critical Reviews--

Page 3 under OTHER PUBLICATIONS, Reference 14, "Myodardial" should be --Myocardial--

Page 3 under OTHER PUBLICATIONS, Reference 19, "Artifical" should be --Artificial--

Column 1, Line 50 "mitrial" should be --mitral--

Column 4, Line 17, "mitrial" should be --mitral--

Column 8, Line 21, "know" should be --known--

UNITED STATES PATENT AND TRADEMARK OFFICE
CERTIFICATE OF CORRECTION

| | |
|---|---|
| PATENT NO. | : 7,300,405 B2 |
| APPLICATION NO. | : 10/781118 |
| DATED | : November 27, 2007 |
| INVENTOR(S) | : Marie A. Guion et al. |

It is certified that error appears in the above-identified patent and that said Letters Patent is hereby corrected as shown below:

Column 13, Line 48, "known to either" should be --known to have either--

Column 14, Line 46, "electrodiagram" should be --electrocardiogram--

Column 15, Line 13, "message comprises;" should be --message comprises:--

Column 15, Line 28, "associate" should be --associated--

Column 16, Line 30, "Thy" should be --T by--

Column 16, Line 31, "tie" should be --the--

Column 16, Line 53, "mitrial" should be --mitral--

Column 16, Line 54, "mitrial" should be --mitral--

Column 17, Line 2, "comprising;" should be --comprising:--

Column 17, Line 4, "patient using an the" should be --patient using the--

Column 17, Line 17, "within multidimensional" should be --within a multidimensional--

Column 17, Line 46, "one or mare" should be --one or more--

Column 19, Line 8, "mitrial" should be --mitral--

Column 19, Line 9, "mitrial" should be --mitral--

UNITED STATES PATENT AND TRADEMARK OFFICE
CERTIFICATE OF CORRECTION

PATENT NO. : 7,300,405 B2
APPLICATION NO. : 10/781118
DATED : November 27, 2007
INVENTOR(S) : Marie A. Guion et al.

It is certified that error appears in the above-identified patent and that said Letters Patent is hereby corrected as shown below:

Column 19, Line 27, "one the physiological" should be --one of the physiological--

Column 20, Line 21, "data mapping" should be --data by mapping--

Column 20, Line 24, "conditions wherein" should be --conditions, wherein--

Signed and Sealed this

Twenty-fourth Day of June, 2008

JON W. DUDAS
*Director of the United States Patent and Trademark Office*